US010400213B2

(12) United States Patent
Evans et al.

(10) Patent No.: US 10,400,213 B2
(45) Date of Patent: Sep. 3, 2019

(54) HIGH EFFICIENCY METHODS OF SEX SORTING SPERM

(71) Applicant: INGURAN, LLC, Navasota, TX (US)

(72) Inventors: Kenneth Michael Evans, College Station, TX (US); Thomas Boyd Gilligan, College Station, TX (US); Johnathan Charles Sharpe, Hamilton (NZ); Juan Moreno, College Station, TX (US); Ramakrishnan Vishwanath, Hamilton (NZ)

(73) Assignee: Inguran, LLC, Navasota, TX (US)

( * ) Notice: Subject to any disclaimer, the term of this patent is extended or adjusted under 35 U.S.C. 154(b) by 0 days.

(21) Appl. No.: 13/784,597

(22) Filed: Mar. 4, 2013

(65) Prior Publication Data

US 2014/0099664 A1    Apr. 10, 2014

Related U.S. Application Data

(60) Provisional application No. 61/710,343, filed on Oct. 5, 2012.

(51) Int. Cl.
*C12N 5/071*    (2010.01)
*C12N 5/076*    (2010.01)
*C12Q 1/6806*    (2018.01)

(52) U.S. Cl.
CPC ........... *C12N 5/061* (2013.01); *C12N 5/0612* (2013.01); *C12Q 1/6806* (2013.01)

(58) Field of Classification Search
USPC .......................................... 435/2, 41, 34, 39
See application file for complete search history.

(56) References Cited

U.S. PATENT DOCUMENTS

| 5,135,759 | A | 8/1992 | Johnson |
| 5,998,212 | A | 12/1999 | Corio et al. |
| 6,149,867 | A | 11/2000 | Seidel et al. |
| 6,263,745 | B1 | 7/2001 | Buchanan et al. |
| 6,524,860 | B1 | 2/2003 | Seidel et al. |
| 6,540,895 | B1 * | 4/2003 | Spence ............. B01L 3/502761 204/450 |
| 7,208,265 | B1 | 4/2007 | Schenk |
| 7,371,517 | B2 | 5/2008 | Evans et al. |
| 7,758,811 | B2 | 7/2010 | Durack et al. |
| 7,799,569 | B2 | 9/2010 | Durak et al. |
| 7,838,210 | B2 | 11/2010 | Ludwig et al. |
| 7,838,509 | B2 | 11/2010 | Ellington et al. |
| 2005/0003472 | A1 | 1/2005 | Anzar et al. |
| 2005/0244805 | A1 | 11/2005 | Ludwig et al. |
| 2006/0067916 | A1 | 3/2006 | Schenk et al. |
| 2006/0121440 | A1 | 6/2006 | Schenk et al. |
| 2007/0117086 | A1 * | 5/2007 | Evans .................. C12N 5/0612 435/4 |
| 2009/0017927 | A1 | 1/2009 | Shozi et al. |
| 2009/0053821 | A1 | 2/2009 | Laikhter et al. |
| 2009/0176271 | A1 * | 7/2009 | Durack ................ C12N 5/0612 435/40.5 |
| 2011/0236923 | A1 | 9/2011 | Hashemi |
| 2014/0099627 | A1 | 4/2014 | Gilligan et al. |
| 2014/0099628 | A1 | 4/2014 | Evans et al. |

FOREIGN PATENT DOCUMENTS

| WO | 1999005504 | A2 | 2/1999 |
| WO | 200137655 | A1 | 5/2001 |
| WO | 0151612 | A1 | 7/2001 |
| WO | 200185913 | A2 | 11/2001 |
| WO | 2004012837 | A3 | 2/2004 |
| WO | 2004104178 | A1 | 12/2004 |
| WO | 2005095960 | A1 | 10/2005 |
| WO | 2009031831 | A2 | 3/2009 |
| WO | 2010021627 | A1 | 2/2010 |
| WO | 2011123166 | A2 | 10/2011 |
| WO | 2012014142 | A1 | 2/2012 |

OTHER PUBLICATIONS

Seidel, et al., "Current Status of Sexing Mammalian Spermatozoa", Reproduction, 2002, 124, pp. 733-743.
International Search Report and Written Opinion dated May 21, 2013, in corresponding PCT Application No. PCT/US2013/28934.
Rath et al., "Improved quality of sex-sorted sperm: A prerequisite for wider commercial application", Theriogenology, 2009, 71, 22-29.
Klinc et al., "Reduction of Oxidative Stress in Bovine Spermatozoa During Flow Cytometric Sorting", Reprod Dom Anim; 2007, 42, 63-67.
Burroughs, C.A.,"Sex-Sorting of Bovine Sperm"Colorado State University, 2011.
De Graaf, S.P., et al., "Application of seminal plasma in sex-sorting and sperm cryopreservation", Theriogenology, 70 2008, 1360-1363.
De Graaf, S.P., et al., "Birth of offspring of pre-determined sex after artificial insemination of frozen-thawed, sex sorted and re-frozen-thawed ram spermatozoa", Theriogenology 67 2007, 391-398.
Garcia, E.M., et al. "Improving the fertilizing ability of sex sorted boar spermatozoa" Theriogenology, 68 2007, 771-778.
Presicce, G.A., et al., "First established pregnancies in Mediterranean Italian buffaloes (*Bubalus bubalis*) following deposition of sexed spermatozoa near the utero tubal junction", Reproduction in Domestic Animals 40.1 (2005): 73-75.

(Continued)

*Primary Examiner* — Nghi V Nguyen
(74) *Attorney, Agent, or Firm* — Ryan Christensen; Hashim Rahman

(57) ABSTRACT

This disclosure relates to cell sorting methods, and particularly cell sorting methods that improve the efficiency or productivity of sorting in a particle sorting instrument utilizing a measured parameter of sorting efficiency. In one embodiment, minimum productivity and minimum purity may be established and maintained while attempting to maximize the sorting efficiency. While in another embodiment, a minimum sorting efficiency and a minimum purity may be established and maintained while attempting to maximize the productivity of a sort.

30 Claims, 7 Drawing Sheets

(56) References Cited

OTHER PUBLICATIONS

U.S. office action dated Dec. 26, 2014 for U.S. Appl. No. 13/784,578.
Underwood et al. "In vitro characteristics of frozen-thawed, sex-sorted bull sperm after refreezing or incubation at 15 or 37° C" Theriogenology (2009) 72: 1001-1008).
Hilinshead et al. "Birth of lambs of a pre-determined sex after in vitro production of embryos using frozen—thawed sex-sorted and re-frozen—thawed ram spermatozoa" Reproduction (2004) 127: 557-568.
Johnson et al., "Improved Flow Sorting Resolution of X- & Y-Chromosome Bearing Viable Sperm Separation Using Dual Staining and Dead Cell Gating." Cytometry, vol. 17, Supplement 7, Abstract, p. 83 (1994).
Strober, Warren. "Trypan blue exclusion test of cell viability", Current protocols in immunology (2001): A-3B.
"Characteristics of Deionised Water", 2004.
US FDC, Food Color Facts, 2007.
Stap et al., "Improving the Resolution of Cryopreserved X- and Y-Sperm During DNA Flow Cytometric Analysis with the Addition of Percoll to Quench the Fluorescence of Dead Sperm" J. Anim. Sci., 1998, 76, 1869, 1902.
Seidel, G.E., Jr., "Sperm sexing technology—The transition to commercial application—An introduction to the Symposium Update on sexing mammalian sperm", Theriogenolgy 71 (2009) 1-3.
U.S. Office Action dated Jul. 18, 2014, issued in corresponding U.S. Appl. No. 13/784,578 (21 pp).
Lardy, et al., (1943). "Effect of pH and certain electrolytes on the metabolism of ejaculated spermatozoa". Am. J. Physiol,138, 741-746.
Johnsi, et al., "Fluorescence Quenching of Tris(2,2'-bipyridine)Ruthenium(II) Dichloride by Certain Organic Dyes", Journal of Solution Chemistry, Oct. 2010, vol. 39, Issue 10, pp. 1520-1530.
Australian Patent Examination Report dated Jun. 26, 2015 in related AU Appl. No. 2013325222.
U.S. office Action dated May 6, 2015 in related U.S. Appl. No. 14/045,617.
New Zealand Patent Examination Report dated Sep. 17, 2015 in related NZ Appl. No. 630388.
U.S. office Action dated Sep. 28, 2015 in related U.S. Appl. No. 14/045,617.
New Zealand Patent Examination Report dated Sep. 17, 2015 in related NZ Appl. No. 630394.
Schenk et al. "Pregnancy Rates in Heifers and Cows with Cryopreserved Sexed Sperm: Effects of Sperm Numbers Per Inseminate, Sorting Pressure and Sperm Storage before Sorting." Theriogenology, 71, 2009, pp. 717-728.
DeJarnette et al. "Evaluating the Success of Sex-Sorted Semen in US Dairy Herds From on Farm Records." Theriogenology, 71, 2009, pp. 49-58.
DeJarnette et al. "Effects of 2.1 and 3.5×106 Sex-Sorted Sperm Dosages on Conception Rates of Holstein Cows and Heifers" J. Dairy Sci. 93, pp. 4079-4085.
DeJarnette et al. "Effects of Sex-Sorting and Sperm Dosage on Conception Rates of Holstein Heifers: Is Comparable Fertility of Sex-Sorted and Conventional Semen Plausible?" J. Dairy Sci. 94, pp. 3477-3483.
Frijters et al. "What Affects Fertility of Sexed Bull Semen More, Low Sperm Dosage or the Sorting Process." Theriogenology, 71, 2009, pp. 64-67.
Featured Charter Sponsor—Dairy Cattle Reproduction Council. 2014. http://www.dcrcouncil.org/newsletters/2014-march/featured-charter-sponsor.aspx.
Australian Patent Examination Report dated Sep. 22, 2015 in related AU Appl. No. 2013325223.
U.S. office Action dated Aug. 13, 2015 in related U.S. Appl. No. 13/784,578.
New Zealand Patent Examination Report dated Sep. 17, 2015 in related NZ Appl. No. 630380.

International Search Report dated May 21, 2013 in related PCT Appl. No. PCT/US13/28931.
International Search Report dated Apr. 22, 2013 in related PCT Appl. No. PCT/US13/63286.
European Search Report dated May 17, 2016 issued in related EP Appl. No. 13844269.4.
Canadian Office Action dated Jan. 18, 2016 issued in related CA Appl. No. 2,886,796.
New Zealand Examination Report dated Jan. 21, 2016 issued in related NZ Appl. No. 630394.
U.S. Office Action dated Jun. 16, 2016 issued in related U.S. Appl. No. 14/045,617.
New Zealand Examination Report dated Jan. 20, 2016 issued in related NZ Appl. No. 630388.
Canadian Office Action dated Jan. 18, 2016 issued in related CA Appl. No. 2,886,782.
European Search Report dated Feb. 22, 2016 issued in related EP Appl. No. 13843780.1.
Johnson, L., et al. "The Beltsville Sperm Sexing Technology: High-Speed Sperm Sorting Gives Improved Sperm Output for In Vitro Fertilization and AI." J. Anim. Sci. vol. 77, Suppl. 2/J Dairy Sci. vol. 82, Suppl. Feb. 1999.
Johnson, L., et al. "Preselection of Sex of Offspring in Swine for Production: Current Status of the Process and its Application." Theriogenology 63 (2005) 615-624.
Rens, Wim, et al. "Improved Flow Cytometric Sorting of X- and Y-Chromosome Bearing Sperm: Substantial Increase in Yield of Sexed Semen." Molecular Reproduction and Development 52:50-56 (1999).
European Search Report dated Jan. 29, 2016 issued in related EP Appl. No. 15186997.1.
Filho, M. et al. "Sex-Sorted Sperm for Artificial Insemination and Embryo Transfer Programs in Cattle." Anim. Reprod., v.11, n.3, p. 217-224, Jul./Sep. 2014.
Gaviraghi, A. et al. "Minimum Number of Spermatozoa Per Dose in Mediterranean Italian Buffalo (*Bubalus bubalis*) Using Sexed Frozen Semen and Conventional Artificial Insemination." Theriogenology 79 (2013) 1171-1176.
Klinc, P. et al. "Insemination with Sex Sorted Fresh Bovine Spermatozoa Processed in the Presence of Antioxidative Substances." Reprod Dom Anim 42, 58-62 (2007).
Vishwanath, R. "Sexed Sperm Vs Conventional Sperm—A Comparative Discussion." Proceedings, Applied Reproductive Strategies in Beef Cattle • Aug. 17 & 18, 2015. http://appliedreprostrategies.com/2015/documents/proceedings/16bVishwanath-pg250-256.pdf.
European Search Report dated Feb. 5, 2016 issued in related EP Appl. No. 13844253.8.
Henkel, Rolf, "Sperm Preparation: State-Of-The-Art—Physiological Aspects and Application of Advanced Sperm Preparation Methods." Asian Journal of Andrology, vol. 14, No. 2, Mar. 1, 2012.
New Zealand Notice of Acceptance dated Apr. 20, 2016 in related NZ Appl. No. 630380.
U.S. Office Action dated Jan. 8, 2016 issued in related U.S. Appl. No. 13/784,578.
Australian Examination Report dated Aug. 30, 2016 issued in related NZ Appl. No. 2013327057.
Canadian Office Action dated Sep. 26, 2016 issued in related CA Appl. No. 2,886,796.
BD Influx Cell Sorter User's Guide; Becton, Dickinson and Company. 2011.
Australian Examination Report dated Apr. 18, 2016 issued in related NZ Appl. No. 2013325223.
Australian Examination Report dated Sep. 13, 2016 issued in related NZ Appl. No. 2013325223.
Canadian Office Action dated Sep. 26, 2016 issued in related CA Appl. No. 2,886,782.
U.S. Office Action dated Oct. 20, 2016 issued in related U.S. Appl. No. 14/045,617.
Australian Examination Report dated Jun. 10, 2016 issued in related NZ Appl. No. 2013325222.
Canadian Office Action dated Jan. 18, 2016 issued in related CA Appl. No. 2,886,903.

(56) References Cited

OTHER PUBLICATIONS

Canadian Office Action dated Sep. 26, 2016 issued in related CA Appl. No. 2,886,903.
New Zealand Notice of Acceptance dated Nov. 7, 2016 in related NZ Appl. No. 630388.
U.S. Office Action dated Nov. 21, 2016 issued in related U.S. Appl. No. 13/784,578.
New Zealand Notice of Acceptance dated Nov. 16, 2016 in related NZ Appl. No. 630394.
Australian Examination Report dated Nov. 24, 2016 issued in related AU Appl. No. 2016231560.
Australian Examination Report dated Dec. 15, 2016 issued in related AU Appl. No. 2013327057.
EP Examination Report dated Jan. 17, 2017 issued in related EP Appl. No. 13844253.8.
U.S. Office Action dated Feb. 17, 2017 in related U.S. Appl. No. 14/045,617.
U.S. Office Action dated Mar. 29, 2017 in related U.S. Appl. No. 14/861,572.
Amirat et al. "Modifications of Bull Spermatozoa Induced by Three Extenders: Biociphos, Low Density Lipoprotein and Triladyl, Before, During and After Freezing and Thawing." Reproduction (2005), v129, p. 535-543.
Kornhauser et al. "Applications of Hydroxy Acids: Classification, Mechanisms, and Photoactivity. Clinical.", Cosmetic and Investigational Dermatology (2010), v3, p. 135-142.
EP Examination Report dated Mar. 20, 2017 in related EP Appl. No. 13843780.1.
U.S. Office Action dated Mar. 16, 2017 in related U.S. Appl. No. 14/784,578.
Paulenz et al. "Comparison of Fertility Results after Vaginal Insemination Using Different Thawing Procedures and Packages for Frozen Ram Semen." Acta Veterinaria Scandinavica 2007, 49:26, 7 pages.
European examination report dated Feb. 2, 2018 in related EP application No. 13844253.8.
U.S. Office Action dated Mar. 13, 2018 in related U.S. Appl. No. 14/861,572.
Australian Notice of Acceptance dated Mar. 14, 2018 in related AU application No. 2015230805.
U.S. Office Action dated Mar. 13, 2018 in related U.S. Appl. No. 13/784,578.
Canadian Requisition by the Examiner dated Aug. 27, 2018 issued in related CA Appl. No. 2,886,782.
U.S. Office Action dated Aug. 10, 2018 issued in related U.S. Appl. No. 14/045,617.
Canadian Requisition by the Examiner dated Aug. 10, 2018 issued in related CA Appl. No. 2,886,903.
AU Notice of Acceptance dated Apr. 18, 2018 in related AU Appl. No. 2017201275.
EP Examination Report dated Jun. 19, 2018 in related EP Appl. No. 15186997.1.
Third Party Observations filed in EPO dated Oct. 1, 2018 issued in related EP Appl. No. 13843780.1.
U.S. office Action dated Aug. 18, 2017 issued in U.S. Appl. No. 14/045,617.
Australian office Action dated May 31, 2017 issued in AU Appl. No. 2016231560.
European Examination Report dated May 16, 2019 issued in related EP Appl. No. 15186997.1.
Chinese Office Action dated Feb. 19, 2019 issued in related CN Appl. No. 20150827567.0.
European Extended Search Report dated Mar. 13, 2019 issued in related EP Appl. No. 19153112.8.
Brazilian Office Action dated Apr. 22, 2019 issued in related BR Appl. No. 112015007479-0.
Brazilian Office Action dated Apr. 22, 2019 issued in related BR Appl. No. 112015007480-4.
U.S. Final Office Action dated Mar. 22, 2019 issued in related U.S. Appl. No. 14/861,572.
United States Office Action dated May 17, 2019 issued in related U.S. Appl. No. 13/784,578.
Gardner et al. Effect on Semen Dilution on Bovine Sperm Viability as Determined by Dual-DNA Staining and Flow Cytometry.Journal of Andrology, 18(3), 324-331. (Year 1997).
U.S. office Action dated Sep. 25, 2017 issued in U.S. Appl. No. 14/861,572.
Juengel et al. Reproduction in Domestic Ruminants VIII (Aug. 2014), i-vi (Year: 2014).
Fouz et al. Factors associated with 56-day non-return rate in dairy cattle. Pesq. agropec. bras., Brasilia (2011), v46(6), (Year: 2011).
De Graaf et al. Reproduction in Domestic Ruminants VIII (Aug. 2014), p. 507-522 (Year: 2014).
U.S. office Action dated Oct. 6, 2017 issued in U.S. Appl. No. 14/784,578.
Canadian office Action dated Sep. 18, 2017 issued in CA Appl. No. 2,886,782.

\* cited by examiner

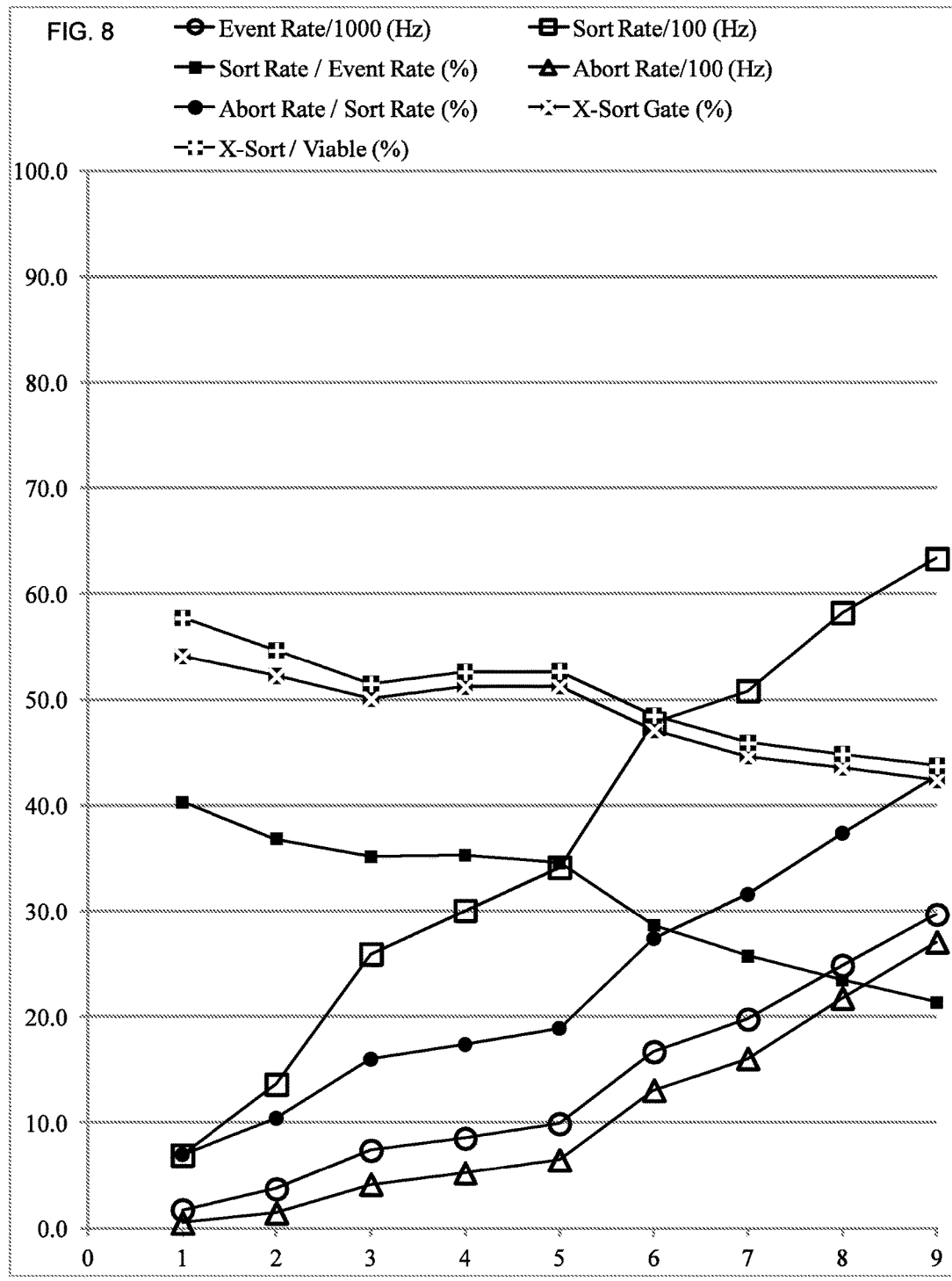

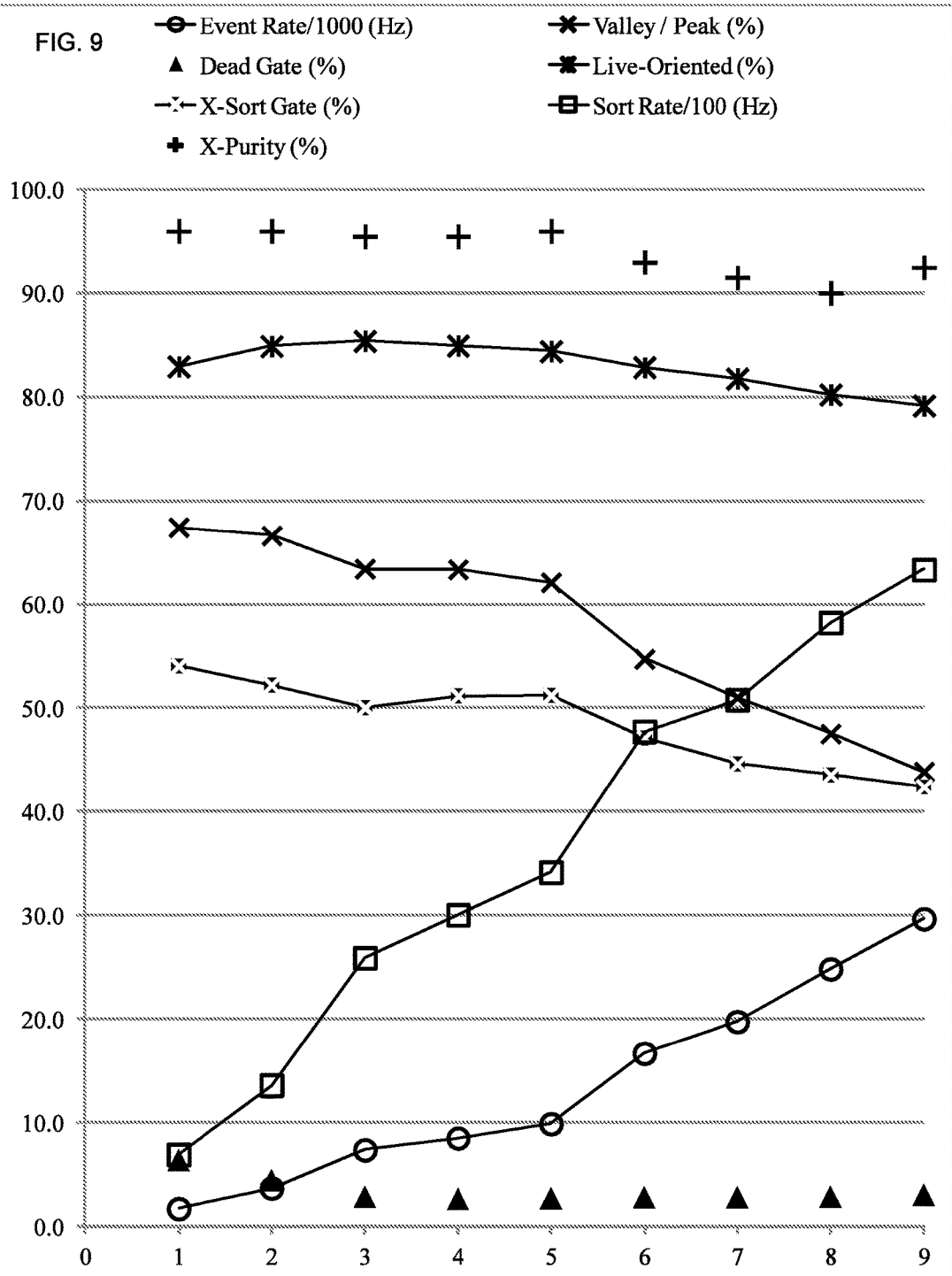

HIGH EFFICIENCY METHODS OF SEX SORTING SPERM

CROSS REFERENCE TO RELATED APPLICATION

This application claims the benefit of U.S. Provisional Patent Application No. 61/710,343 filed on Oct. 5, 2012, the entire contents of which are incorporated herein by reference.

TECHNICAL FIELD

Generally, this disclosure relates to cell sorting methods, and more particularly relates to sorting methods that improve the efficiency and recovery of sex sorted sperm.

BACKGROUND

The most widely used sperm sorting methods generally rely on the detection of quantifiable differences in the DNA content of X-chromosome bearing sperm and Y-chromosome bearing sperm. Various modifications to flow cytometers for this purpose have been described in U.S. Pat. Nos. 5,135,759, 6,263,745, 7,371,517 and 7,758,811, each of which are incorporated herein by reference. In many species, this difference in DNA content can be small. In bovine, for example, Holstein bulls have about a 3.8% difference in DNA content, while Jersey bulls have about a 4.1% difference. The inexact nature of stoichiometric DNA staining makes these small differences difficult to ascertain and requires exposing sperm to damaging conditions over periods of time.

While Hoechst 33342 can be used in non-toxic concentrations, sperm must be incubated at elevated temperatures and elevated pHs for sufficient Hoechst 33342 penetration with sufficient uniformity for analysis or sorting. Each of elevating sperm temperature and changing the sperm pH may contribute to sperm damage. Additionally, the pressure and sheering forces applied to sperm cells within a flow cytometer may further compromise sperm membranes. These factors may accelerate the deterioration of sperm cell membranes further reducing the already limited shelf life of viable sperm.

Accordingly, previous sperm sorting efforts focused on utilizing smaller insemination samples and producing the greatest amount of sorted sperm in the shortest amount of time. U.S. Pat. No. 6,149,867, incorporated herein by reference, describes methods and devices geared towards helping sperm better survive flow cytometric sorting in combination with reduced dosage inseminates. Subsequent advances in flow sorting focused on improvements in detection or throughput. However, as speeds and throughputs increased, larger quantities of sperm, including viable sperm of the desired sex, are discarded with waste. Additional tradeoffs between purity and recovery also exist. For example, where the desirable purity is greater than 95%, fewer sperm can be determined with the requisite confidence level as compared to 70% 80% or 90% purities, meaning fewer sperm are sorted at increasingly high purities and that more viable sperm cells are disposed with the waste stream.

Additional losses in efficiency exist with respect to discarding viable sperm cells due to the occurrence of coincident events. A coincident event occurs when two or more sperm cells are too close together to be separated. In either event, all of the sperm cells may be discarded with waste, whereas some or all of those discarded cells may have been desirable to collect.

Previously, recovery problems were often overlooked, or moot, in view of raw flow sorting throughput. Bovine sperm, for example, is relatively easy to collect and process and high purities may be desirable in both the beef and dairy industries, even at the expense of discarding as much as about 90% of the sperm. However, this high throughput methodology is not acceptable for sperm in limited supply. For example, a specific animal could possess exceptionally desirable genetic qualities, but may produce poor sperm samples for sorting. A species could be rare, endangered, or difficult to collect, limiting the amount of sperm available for sorting. A previously collected sample may be preserved, but the animal or species may no longer be available for subsequent collections. Regardless of the circumstances, the wasteful sperm sorting process is undesirable for sperm in limited supply or sperm with high value. A need, therefore, exists for a method of sorting viable sperm with an improved efficiency in recovering sperm cells.

SUMMARY OF THE INVENTION

Certain embodiments of the claimed invention are summarized below. These embodiments are not intended to limit the scope of the claimed invention, but rather serve as brief descriptions of possible forms of the invention. The invention may encompass a variety of forms which differ from these summaries.

One embodiment relates to a method of efficiently sorting a sperm sample in a particle sorting instrument. The method may begin with the step of establishing a sheath fluid stream in the particle sorting instrument and flowing a sperm sample into the sheath fluid stream. Sperm can be oriented with the particle sorting instrument which may also differentiate viable X-chromosome bearing sperm and/or viable Y-chromosome bearing sperm from the remainder of the sample. Viable X-chromosome bearing sperm and/or the viable Y-chromosome bearing sperm may then be collected. One or more measured sorting parameters in the particle sorting instrument may be determined in the particle sorting instrument. A minimum productivity and a minimum purity may be established for the sort and a sorting efficiency may be determined from the measured sorting parameters determined while sorting. One or more of the instrument parameters may be adjusted to increase the sorting efficiency while maintaining the minimum productivity and maintaining the minimum purity.

Another embodiment relates to a method of efficiently sorting a sperm sample in a particle sorting instrument which may begin with the step of establishing a sheath fluid stream in the particle sorting instrument. A sperm sample may be flowed into the sheath fluid stream. Sperm may be oriented with the particle sorting instrument and then differentiated from the remainder of the sample as viable X-chromosome bearing sperm and/or viable-Y chromosome bearing sperm. Viable X-chromosome bearing sperm and/or the viable Y-chromosome bearing sperm may then be collected. One or more measured sorting parameters may be determined in the particle sorting instrument. A minimum sorting efficiency and a minimum purity may be established. A productivity may be determined based on measured sorting parameters during sorting. One or more of the instrument parameters may then be adjusted to increase the productivity while maintaining a minimum sorting efficiency and maintaining a minimum purity.

Still another embodiment relates to a method of efficiently sorting a sperm sample. The method may begin with the steps of standardizing the concentration of a sperm sample and standardizing the pH of a sperm sample and may continue with staining the sperm sample with a single dilution to provide a stained sperm sample having a concentration between about $160 \times 10^6$ sperm cells per microliter and about $640 \times 10^6$ sperm cells per microliter. Sperm may be analyzed in a particle sorting instrument which is operated in a mode that aborts sorting any coincident events while achieving at least 90% purity. Viable X-chromosome bearing sperm and/or viable Y-chromosome bearing sperm may then be collected. Between about 25 percent and 50 percent of the sperm sample processed through the particle sorting instrument may be sorted or collected into an enriched X-chromosome bearing sperm population and/or in an enriched Y-chromosome bearing sperm population.

BRIEF DESCRIPTION OF THE DRAWINGS

FIG. 8 illustrates a graphical representation of data produced in accordance with embodiments described herein.

FIG. 9 illustrates a graphical representation of data produced in accordance with embodiments described herein.

Figure 1:
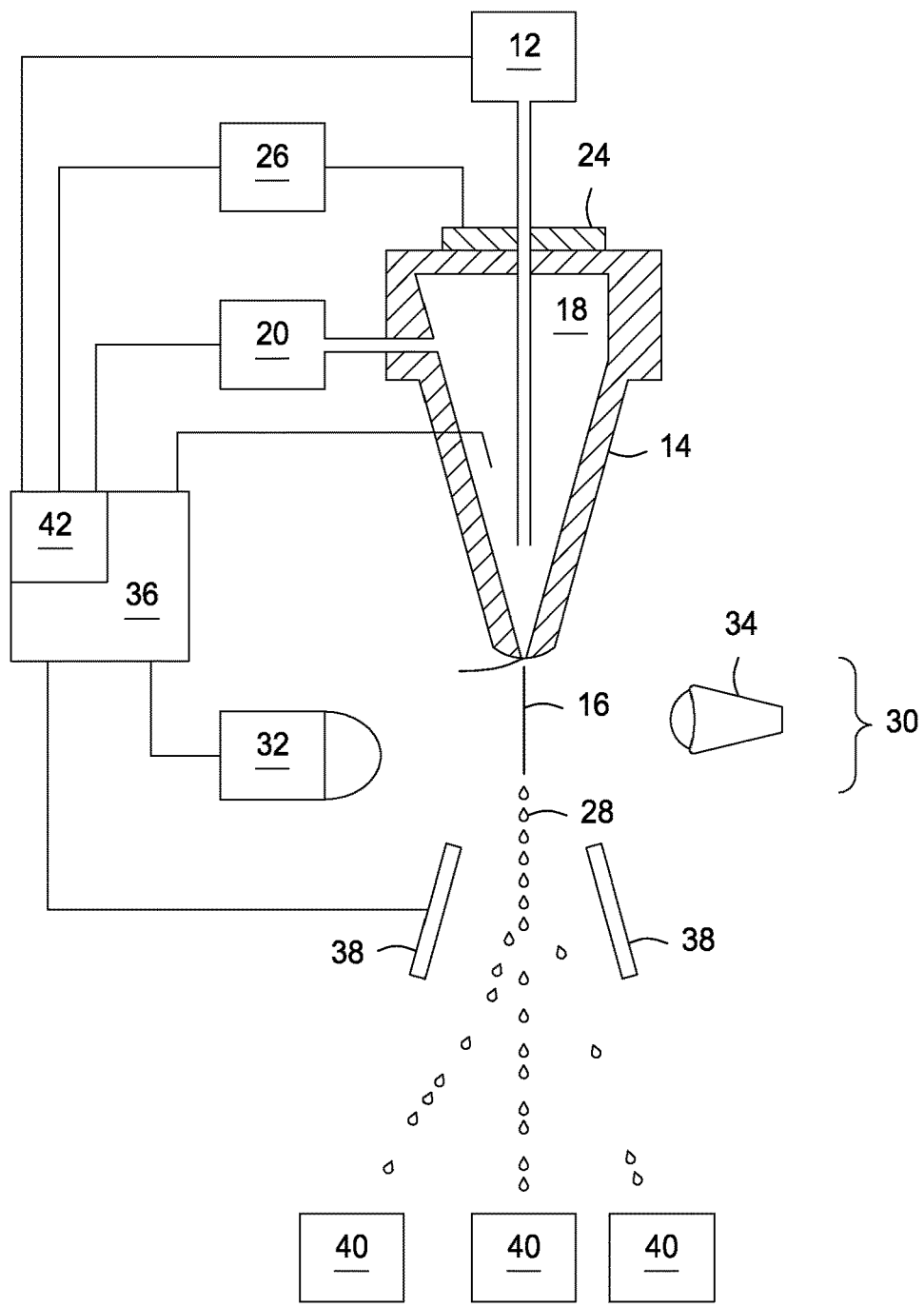
FIG. 1 illustrates a schematic of a flow cytometer for sorting sperm in accordance with certain embodiments described herein.

While the present invention may be embodied with various modifications and alternative forms, specific embodiments are illustrated in the figures and described herein by way of illustrative examples. It should be understood the figures and detailed descriptions are not intended to limit the scope of the invention to the particular form disclosed, but that all modifications, alternatives, and equivalents falling within the spirit and scope of the claims are intended to be covered.

MODES FOR CARRYING OUT THE INVENTION

As used herein, the term "instrument parameter" should be understood to include settings relating to the analyzing and/or sorting conditions in, of, and relating to an instrument, where such settings may be modified by manual or automatic adjustments to the instrument. In the case of a flow cytometer, or other similar instruments, the instrument parameters may include, sample pressure, sample flow rate, sheath pressure, sheath flow rate, drop drive frequency, drop drive amplitude, coincidence abort logic, gating regions, sorting logic, and other similar settings.

The term "sorting parameters" may include those conditions relating to sorting preformed in a particle sorting instrument. Sorting parameters may include measured sorting parameters in addition to parameters which are determined offline, estimated by an operator, and conditions relating to a sorted population of particles or cells.

"Measured sorting parameters" may include those conditions relating to sorting measured directly, calculated, or determined in a particle sorting instrument while analyzing and/or sorting a population of particles or cells. In the case of a flow cytometer, or other similar instruments, the measured sorting parameters may include: event rate; sort rate; sorting efficiency; abort rate; dead gate percentage; live oriented gate percentage; valley to peak ratio; or the percentage of events in other sorting gates, such as an X-sort gate or a Y-sort gate.

As used herein the term "coincidence event" may be understood as a single event in a particle sorting instrument where one or more particles or cells are too close to be separated for individual collection, and where only one of the two cells or particles is desirable for collection. In the case of a droplet sorting jet-in-air flow cytometer, a coincident event may occur when two sperm cells are close enough such that they will end up in the same droplet but only one of those two cells is desired for collection. In a microfluidic chip or fluid switching sorter, a coincident event may occur when two particles or cells are so close that any mechanism to change particle trajectory will be deflected both particles together, when only one of the particles is desirable for collection.

The term "sorting efficiency" may be understood to refer to the recovery particles or cells in terms of the percentage of particles or cells sorted or collected out of a group of cells or particles which are analyzed. The analyzed group of cells may be the total number of cells analyzed or may be a subset of the total number of cells analyzed, such as the analyzed cells determined to be viable or otherwise desirable for analysis and potential collection.

With respect to sorting, the term "productivity," as used herein may be understood to refer to the number of sorted or collected particles or cells per unit time.

With respect to sorting, the term "purity" may refer to an actual or estimated percentage of cells or particles in the population of collected or sorted particles or cells having the characteristic for which the particles were sorted. In the case of sperm, purity may refer to the percentage of X-chromosome bearing sperm in a population sorted for X-chromosome bearing sperm or the percentage of Y-chromosome bearing sperm in a population sorted for Y-chromosome bearing sperm regardless of the viability of the sorted sperm.

Certain aspects disclosed herein relate to a method of efficiently sorting a sperm sample in a particle sorting instrument. Particle sorting instruments may include jet-in-air flow cytometers, such as the MoFlo SX, MoFlo XDP (Beckman Coulter, Miami Fla., USA); however, other commercially available flow cytometers could be modified for sperm sorting as well. The jet-in-air flow cytometers may be outfitted with orienting features such as, orienting nozzles for orienting sperm, optics for uniformly illuminating cells, and/or radially uniform optics for collecting fluorescence emissions from all cells regardless of their orientation. Cytometers having different flow chambers may also be used, such as flow cytometers with closed chambers, or cuvettes. Additionally, devices such as microfluidic chips with sorting functions may be used in accordance with certain embodiments described herein.

Some embodiments described herein relate to the tracking and/or optimization of sorting efficiency, while other embodiments described herein relate to tracking sorting efficiency and maintaining at least a minimum threshold of sorting efficiency. Both embodiments introduce the new measured parameter of sorting efficiency into particle sorting devices. In the case of sperm, sorting efficiency may be the percentage of sperm collected in a sorted group as compared to the total number of sperm analyzed, or the percentage of sperm collected as compared to the total number of analyzed sperm determined to be viable sperm. When sorting efficiency is viewed in terms of the percentage of sperm collected to the total population of sperm analyzed, it can be understood dead sperm, or sperm characterized as membrane compromised or non-viable, may contribute to significant losses in sorting efficiency.

One embodiment described herein provides a synergistic combination including staining methodologies which may reduce the numbers of dead sperm cells and which, in some cases, may improve a flow cytometers ability to differentiate X-chromosomes bearing and Y-chromosome bearing sperm. Such a synergistic combination provides a methodology for drastically reducing the amount of discarded sperm of a desired sex which may have previously been discarded as dead or unoriented. Yet another beneficial aspect of the improved staining methodology provides sperm at higher concentrations for sorting than previous two step staining procedures. As will be described further below, the higher concentrations of sperm may provide good event rates for acceptable productivity even when operating at high purities and low sample fluid flow rates, which may further improve sperm alignment and orientation.

Certain aspects of this disclosure provide methods for improving the efficiency with which a sample is sorted, while operating in a mode where all coincident events are rejected. Previous methodologies may have suggested recovery can be improved by operating flow cytometers in a mode that accepts all coincident events. A coincident event can be understood as a particle detected in a flow cytometer that cannot be separated from an undesirable particle, where the undesired particle may be a particle of the wrong sex, a dead particle, an unoriented particle, or an otherwise unidentifiable particle which would not be collected. A common example would be the case of a desirable particle and an undesirable particle being placed within the same droplet. Most flow cytometers abort such particles in the interest of preserving the purity of the sorted sperm sample.

Obtaining and Staining Sperm for Sorting

A population of sperm can be obtained in the form of neat semen, extended sperm, frozen-thawed sperm or in combinations thereof. The population of sperm can be obtained at the same location the remaining steps are performed, or can be extended in an appropriate sperm buffer for transport to a sorting facility. Once obtained, the sperm can be maintained at room temperature, chilled, or even frozen in an appropriate buffer for later use. Sperm for staining and sorting may be acquiring from a mammal, or may be acquired sperm from storage, such as a frozen or chilled straw obtained from storage. Alternatively, frozen or extended sperm may be pooled.

The population of sperm can originate from mammals, such as a non-human mammals listed by Wilson, D. E. and Reeder, D. M., *Mammal Species of the World*, Smithsonian Institution Press, (1993), the entire contents of which are incorporated herein by reference.

At the time of collection, or thawing, or even pooling, sperm may be checked for concentration, pH, motility, and/or morphology. Additionally, antibiotics may be added prior to further processing steps.

Once obtained, sperm may optionally be standardized to a predetermined concentration and/or towards a predetermined pH. Each of the predetermined concentration and pH may be specific to different species, or even to different breeds of animals within a species. In one embodiment, the sperm may be combined with an initial buffer in the form of a high capacity buffer. Exemplary buffers may include TRIS citrate, sodium citrate, sodium bicarbonate, HEPES, TRIS, TEST, MOPS, KMT, TALP, and combinations thereof. Any buffer having a high capacity for buffering pH may also be employed, and may be used in combination with additional components which promote sperm viability such as egg yolk, and sources of citrates or citric acid. Additionally, antioxidants and antibiotics may be employed in the initial buffer to promote sperm viability.

The initial buffer may be set at a predetermined pH to normalize the pH of all the obtained sperm samples. In one embodiment, the buffer is adjusted to a pH of 7.2. Additionally, semen may become increasingly acidic over time, possibly due to proteins in the seminal fluid, or due to acidic byproducts of dying or dead cells. The initial buffer introduces enough free proton (i.e $H^+$) binding sites to maintain pH near the predetermined target. Even in light of the natural tendency for sperm to become more acidic over time, the initial buffer provides a means for stabilizing pH throughout additional processing steps.

As one example, the sperm sample may be diluted in the high capacity buffer in ratios from about 1:1 to about 1:10. The resulting mixture will have a sperm concentration many times below natural sperm concentrations for a particular species. The extended sperm may be centrifuged in order to reconcentrate sperm. Centrifuging the sperm and removing supernatant allows the sperm to be reconcentrated into a predetermined concentration. The predetermined concentration may be selected based on additional sperm processing steps. For example, in the case of sex sorting bovine, sperm may be reconcentrated at between about 2400 million sperm per ml and about 900 million sperm per ml to simulate a natural range of concentrations. Other concentrations, such as between about 1400 million sperm per ml and about 2100 million sperm per ml, or between about 1700 million sperm per ml and about 2100 million sperm per ml may also be achieved for further processing.

Adjusting the sperm concentration and pH may provide a uniform starting point for further processing. For example, a relatively consistent pH and concentration may provide greater predictability in staining sperm, for example with a DNA selective dye. If each sample is adjusted to the same predetermined pH and concentration, fewer trials may be required on each new collection to ensure adequate staining for sex sorting.

The population of sperm will include X-chromosome bearing sperm and Y-chromosome bearing sperm. Additionally, each of the X-chromosome bearing sperm and the Y-chromosome bearing sperm will include viable sperm and nonviable sperm. Viable sperm can be considered sperm with intact membranes while nonviable sperm can be considered sperm with compromised membranes. The distinction between viable sperm and non-viable sperm in conventional sperm sorting is determined with the inclusion of a quenching dye that permeates membrane compromised sperm. Sperm which tends to be dead or dying absorbs the quenching dye and produces fluorescence signals distinct from the remaining sperm population, whereas sperm cells having intact membranes tend to be viable sperm cells that will prevent uptake of the quenching dye. Viable sperm, in the appropriate dosage, will generally be capable of achieving fertilization in an artificial insemination, while nonviable sperm, or membrane compromised sperm, may be incapable of achieving fertilization in an artificial insemination or will have a greatly reduced ability to do so. However, some sperm capable of fertilization may have compromised membranes, and some sperm with intact membranes may be incapable of fertilization.

Whether standardized or not, sperm may be stained with a staining buffer for introducing a DNA selective dye. In the staining step, at least a portion of the population of sperm is incubated with a staining buffer and a DNA selective fluorescent dye in order to stoichiometrically stain the DNA content of each cell in the sperm population. Hoechst 33342 tends to be less toxic than other DNA selective dyes. The vehicle for delivering this dye may be in the form of a modified TALP buffer adjusted to a pH of about 7.4. Hoechst 33342 is described in U.S. Pat. No. 5,135,759 and is commonly used for this purpose. However, other UV excitable dyes, as well as visible light excitable dyes, fluorescent polyamides, fluorescent nucleotide sequences, and sex specific antibodies could also be used.

Sperm in a natural state is often not readily permeable to such dyes. In order to produce a uniform staining, the first step of staining can include incubating at least a portion of the sperm population at an elevated temperature in a staining buffer at an elevated pH in addition to the dye. Examples of appropriate first staining buffers can be a TALP, TES-TRIS, TRIS citrate, sodium citrate, or a HEPES based medium, each described in WO2005/095960, incorporated herein by reference. An exemplary modified TALP described in WO2001/37655, incorporated herein by reference, is illustrated in Table 1.

TABLE 1

Modified TALP buffer

| Ingredient | Concentration |
|---|---|
| NaCl | 95.0 mM |
| KCl | 3.0 mM |
| NaHPO$_4$ | 0.3 mM |
| NaHCO$_3$ | 10.0 mM |
| MgCL$_2$ 6H$_2$O | 0.4 mM |
| Na Pyruvate | 2.0 mM |
| Glucose | 5.0 mM |
| Na Lactate | 25.0 mM |
| HEPES | 40.0 mM |
| bovine serum albumin | 3.0 mg/ml |

As one example, the population of sperm, or a portion of the population of sperm, could be diluted with the first buffer to between 640×10$^6$ and 40×10$^6$ sperm/ml, to between about 320×10$^6$ and 80×10$^6$ sperm/ml, or to about 160×10$^6$ sperm/ml in the first buffer. The DNA selective fluorescent dye can be added to the sperm suspended in the first buffer in a concentration of between about 10 μM and 200 μM; between about 20 μM and 100 μM, or between about 30 μM and 70 μM. The pH of the first buffer can be between about 6.8 and 7.9; about 7.1 and 7.6; or at about 7.4 in order to help ensure a uniform staining of nuclear DNA. Those of ordinary skill in the art will appreciate the pH can be elevated with the addition of NaOH and dropped with the addition of HCl.

The population of sperm can be incubated between 30-39° C., between about 32-37° C., or at about 34° C. The period of incubation can range between about 20 minutes and about an hour and a half, between about 30 minutes and about 75 minutes, or for about 45 minutes to about 60 minutes. As one example, the population of sperm can be incubated for about 45 minutes at 34° C. Even within a single species, sperm concentration and pH and other factors affecting stainability can vary from animal to animal. Those of ordinary skill in the art can appreciate minor variations for incubating sperm between species and even between breeds or animals of the same breed to achieve uniform staining without over staining a population of sperm.

In addition to the DNA selective fluorescent dye, a quenching dye may be applied for the purpose of permeating membrane compromised sperm and quenching the signals they produce. A dead quenching dye can be understood to include dyes which differentially associate with membrane compromised sperm. It may be that these dyes enter membrane compromised sperm cells more easily because the membranes are breaking down or otherwise increasingly porous. It may also be that dead quenching dyes readily enter all sperm cells and that healthy sperm cells act to pump dead quenching dyes out faster than membrane compromised sperm. In either case, the sperm cells with which the dead quenching dyes associate includes a large portion of dead and dying sperm cells, although not necessarily all dead and dying sperm cells. The quenched signals produced from membrane compromised sperm having an association with quenching dye are distinct enough from the signals of healthy sperm that they may be removed from the further analysis and sorting applied to viable sperm.

In one embodiment, a second staining step is preformed which further reduces the concentration of sperm and introduces the dead quenching dye. The pH of the second staining solution may be targeted to achieve a target pH in the final sperm sample. Exemplary descriptions of two step staining processes are described in published PCT International Application WO 2011/123166 and International Application PCT/US12/58008, the entire disclosure of both are incorporated herein by reference.

In another embodiment, the quenching dye and the DNA selective dye are applied together in a single treatment. In this embodiment, the quenching dye is incubated along with the DNA selective dye at an elevated temperature in the modified TALP which may be at a pH of 7.4. In this embodiment, it is believed a synergy exists when the sperm is standardized at an elevated pH of about 7.2 before staining at 7.4. In this way, the pH to which the sperm is exposed remains in a constant range with minimal variations. Because both the staining buffer and the initial extender have high buffering capacities, it is believed the natural tendency of sperm to become more acidic over time will be avoided. Additionally, by minimizing the changes in pH seen by the sperm, it is believed the sperm are in a healthier condition to face the various pressures and stresses endured in the sex sorting process.

Sorting Stained Sperm

Previously, particle sorting instruments operated for the purpose of sorting sperm relied on the principal of achieving high levels of productivity in terms of sperm sorted per second. However, high efficiency sorting may be performed on such a machine with the goal of recovering as large of a portion of the desired sperm cells as is possible. Whereas previous focuses on productivity and/or purity failed to achieve significant efficiency with an ejaculate. For example, a MoFlo XDP, available from Beckman Coulter (Miami Fla., USA) may be set to event rates of about 40,000 events per second, for achieving between about 4,000 and about 8,000 sorts per second, while achieving 90 percent purity. However, higher productivity (sort rates) may be achieved at the expense of one or both of purity and efficiency. In a synergistic combination with improved staining methods, higher sperm concentrations, and lower dead gates provide a vehicle for improving sort rates while maintaining improved sorting efficiency and standard purities.

Whether standardized or not and whether stained on a single step or in two steps, the sperm population can be sorted by a particle sorting instrument, such as flow cytometer. Referring to FIG. 1, a jet-in-air flow cytometer (10) is illustrated, although sorting may be performed with microfluidic chips or other types of flow cytometers, including flow cytometer having closed chambers and cytometers and cytometers incorporating ablating lasers. The flow cytometer (10) includes a cell source (12) for producing a flow of sperm sample, such as a flow of stained sperm sample, for sorting. The rate at which the sperm sample is delivered to the nozzle (14) may be considered the sample flow rate, and may be determined by a sample pressure applied at the cell source (12). The flow of stained sperm sample is deposited within a nozzle (14) and introduced into, or flowed into, a fluid stream (16) of sheath fluid (18). The sheath fluid (18) can be supplied by a sheath fluid source (20) so that as the cell source (12) supplies the sperm into the sheath fluid (18) they are concurrently fed through the nozzle (14). The sheath fluid (18) may be supplied at a sheath flow rate which is determined by a sheath pressure applied at the sheath fluid source (20). In this manner the sheath fluid (18) forms a fluid stream coaxially surrounding the sample having stained sperm which exits the nozzle (14) at the nozzle orifice (22). By providing an oscillator (24) which may be precisely controlled with an oscillator control (26), pressure waves may be established within the nozzle (14) and transmitted to the fluids exiting the nozzle (14) at nozzle orifice (22). In response to the pressure waves, the fluid stream (16) exiting the nozzle orifice (22) eventually forms regular droplets (28) at precise intervals. The frequency, and to some extent the shape of the formed droplets may be controlled by a drop drive frequency and drop drive amplitude supplied to the oscillator (24) or the oscillator controller (26).

Each droplet, so formed, retains the sheath fluid and sperm sample that previously formed a portion of the fluid stream (16). Because the stained sperm are surrounded by the fluid stream (16) or sheath fluid environment, the droplets (28) ideally contain individually isolated sperm. However, the sample concentration, sample pressure, and other instrument parameters dictate the frequency with which multiple cells will regularly occupy a single droplet, as well as the percentage of droplets containing sperm cells.

The flow cytometer (10) acts to sort droplets based on the characteristics of sperm predicted to be contained within the droplets. This can be accomplished through a cell sensing system (30) in communication with an analyzer (36). The cell sensing system (30) includes at least one sensor (32) responsive to the cells contained within fluid stream (16). The cell sensing system (30) provides data to the analyzer (36), which may cause an action depending upon the relative presence or relative absence of a characteristic of cells in the fluid stream (16). Certain characteristics, such as the relative DNA content of sperm cells, can be detected through excitation with an electromagnetic radiation source (34), such as a laser generating an irradiation beam to which the stained sperm are responsive. The electromagnetic radiation source (34) can be a laser operated at UV wavelength, such as at about 355 nm. An example of such a laser can be a Vanguard 350 (available from Spectra-Physics), which operates at 350 mW. Various optics may be employed to shape the beam profile of the laser, split the beam to more than one stream, or reduce the beam power at a stream. Non-limiting examples of such optics can be found in WO/2004/104178 and WO/2001/85913, each being incorporated herein by reference.

The characteristics of individual sperm, particularly the presence of an X-chromosome or a Y-chromosome can be determined from the detected fluorescence produced in response to the electromagnetic radiation source (34). In particular, configurations of the cell sensing system (30) may be in communication with an analyzer for providing a variety of fluorescence in formation, such as the forward fluorescence of an event, the side fluorescence of an event, or the amount of scatter associated with an event. The analyzer (36) may include written instructions for analyzing the signals produced by the one or more sensors (32) in the cell sensing system (30). The DNA selective fluorescent dye binds stoichiometrically to sperm DNA. Because X-chromosome bearing sperm contain more DNA than Y-chromosome bearing sperm, the X-chromosome bearing sperm can bind a greater amount of DNA selective fluorescent dye than Y-chromosome bearing sperm. Thus, by measuring the fluorescence emitted by the bound dye upon excitation, it is possible to differentiate between X-bearing spermatozoa and Y-bearing spermatozoa. Distinctions, such as sperm which is viable or not viable, may be differentiated in addition to oriented and unoriented sperm by the analyzer (36) according to sorting logic incorporated gating regions.

In order to achieve separation and isolation based upon stained sperm characteristics, emitted light can be detected by the sensor (32) and the information fed to an analyzer (36) coupled to a droplet charger which differentially charges each droplet (28) based upon the characteristics of the stained sperm contained within that droplet (28). In this manner the analyzer (36) acts to permit the electrostatic deflection plates (38) to deflect droplets (28) based on whether or not they contain the appropriate particle or cell.

As a result, the flow cytometer (10) acts to separate stained sperm by causing the droplets (28) containing sperm to be directed to one or more collection containers (40). For example, when the analyzer differentiates sperm cells based upon a sperm cell characteristic, the droplets entraining X-chromosome bearing spermatozoa can be charged positively and thus deflect in one direction, while the droplets entraining Y-chromosome bearing spermatozoa can be charged negatively and thus deflect the other way, and the wasted stream (that is droplets that do not entrain a particle or cell or entrain undesired or unsortable cells) can be left uncharged and thus is collected in an undeflected stream into a suction tube or the like. Alternatively, one of the X-chromosome bearing sperm or the Y-chromosome bearing sperm may be collected, while the other is discarded with waste.

A controller (42) may form a portion of the analyzer (36) or may be a component external to the analyzer (36). The illustrated controller (42) may also represent a collection of individual controllers. The controller (42) may receive signals or instructions from the analyzer (36) and in response may modify one or more instrument parameters, such as the sample flow rate, sample pressure, sheath flow rate, sheath pressure, drop drive frequency, or drop drive amplitude and the like. The controller (42) may also provide an interface for operator input to manually adjust the sample flow rate, sample pressure, sheath flow rate, sheath pressure, drop drive frequency, drop drive amplitude and the like. The analyzer (36) may include written instructions for modifying the instrument parameters in response to measured sorting parameters, or modifications to instrument parameters may be manually performed by an operator adjusting various settings. The modifications to instrument parameters may be carried out in the analyzer (36) such as for changing sorting logic, abort logic, sorting regions, or gate regions and other parameters specific to making sort decisions in the analyzer. Additional modifications to instrument parameters may be effected by a controller (42), for controlling various external components to the analyzer, such as for controlling the sample pressure, sample flow rate, sheath pressure, sheath flow rate, drop drive frequency, and drop drive amplitude.

Figure 2:
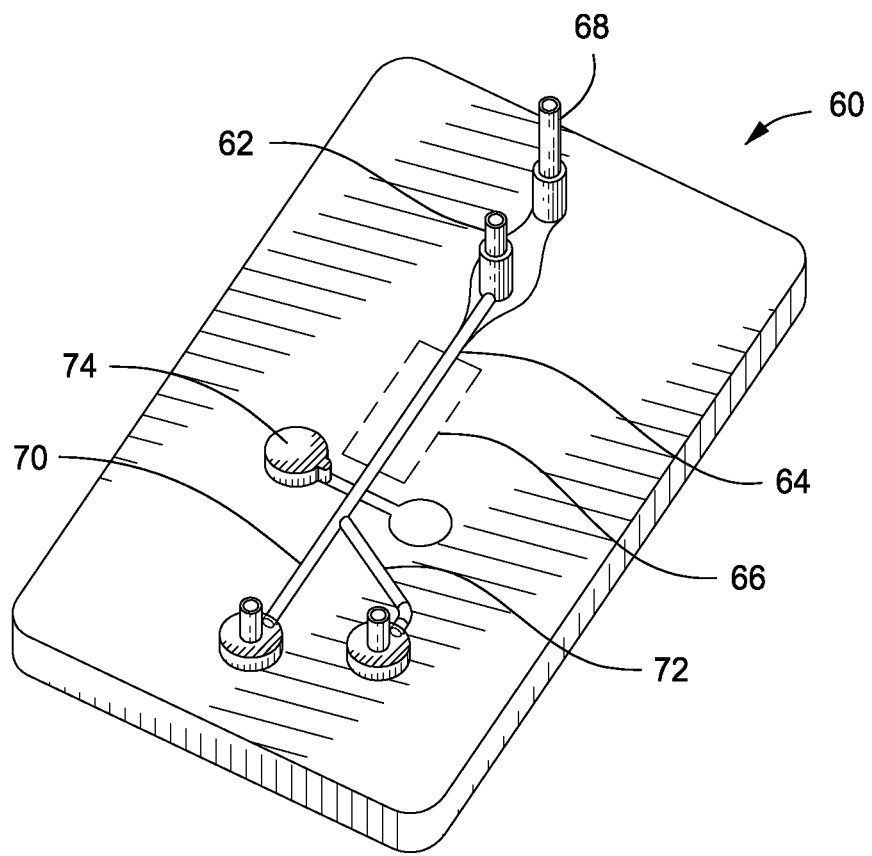
FIG. 2 illustrates a schematic of a microfluidic chip for sorting sperm in accordance with certain embodiments described herein.

Turning now to FIG. 2 an alternative particle sorting instrument is partially illustrated in the form of a microfluidic chip (60). The microfluidic chip (60) may include a sample inlet (62) for introducing sample containing particles or cells into a fluid chamber (64) and through an inspection zone (66). Sample introduced through the sample inlet (62) may be insulated from interior channel walls and/or hydrodynamically focused with a sheath fluid introduced through a sheath inlet (68). Sample may be interrogated at the inspection zone (66) with an electromagnetic radiation source (34), such as a laser, arc lamp, or other source of electromagnetic electricity. Resulting emitted or reflected light may be detected by a sensor (32) and analyzed with an analyzer (36), like that in described in FIG. 1. Each of the sheath pressure, sample pressure, sheath flow rate, and sample flow rate in the microfluidic chip may be manipulated in a manner similar to a jet-in-air flow cytometer, by either automatic adjustments performed by the execution of written instructions in the analyzer (36) or by manual adjustments performed by an operator.

Once inspected, particles or cells in the fluid chamber (64) may be mechanically diverted from a first flow path (70) to a second flow path (72) with a separator (74), for altering fluid pressure or diverting fluid flow. The particles or cells may also be permitted to continue flowing along the first flow path (70) for collection. The illustrated separator (74) comprises a membrane which, when depressed, may divert particles into the second flow path (72). Other mechanical or electro-mechanical switching devices such as transducers and switches may also be used to divert particle flow.

Figure 3:
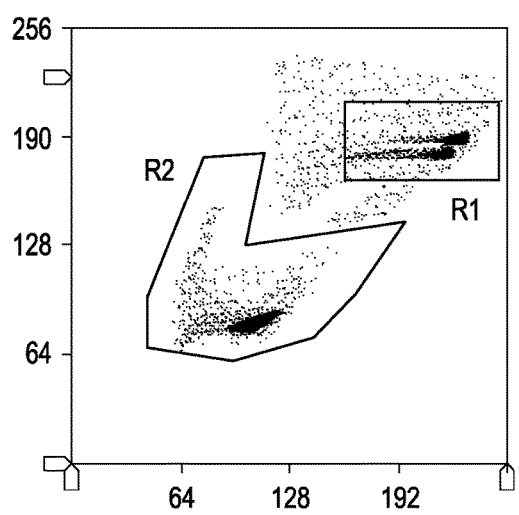
FIG. 3 illustrates a graphical representation of various sort parameters acquired in a flow cytometer while sorting sperm according to various embodiments described herein.

FIG. 3 illustrates a representative bivariate plot of side fluorescence and forward fluorescence from a jet-in-air flow cytometer of stained sperm, which may be generated by an analyzer (36). The visual representation of data may be used by an operator to receive feedback relating to the sample undergoing sorting and to graphically demonstrate certain aspects of the current sorting logic. R1, for example, can be seen as a gating region which may be applied to the sort logic of the flow cytometer. Additional numerical output may be provided in a display of the analyzer (36). Such numerical output may be in the form of measured sorting parameters, such as an event rate, an abort rate, sort rate, sorting efficiency, or the percentage of particles in any region or gate. R1 is illustrated as a region which may be considered the live oriented region, because the boundaries of R1 include two dense populations of cells which reflect a closely related X-chromosome bearing population of sperm and Y-chromosome bearing population of sperm. R2 is a gating region set around the non-viable sperm cells, or the membrane compromised sperm cells whose fluorescence is quenched by a dead quenching dye. While a variety of sort logics may be employed, two strategies relating to R1 and R2 might be a first step in a sorting logic whereby all events falling in R1 are accepted for further processing or gating. Alternatively all events falling outside of R2 are accepted for further processing or gating.

Figure 4:
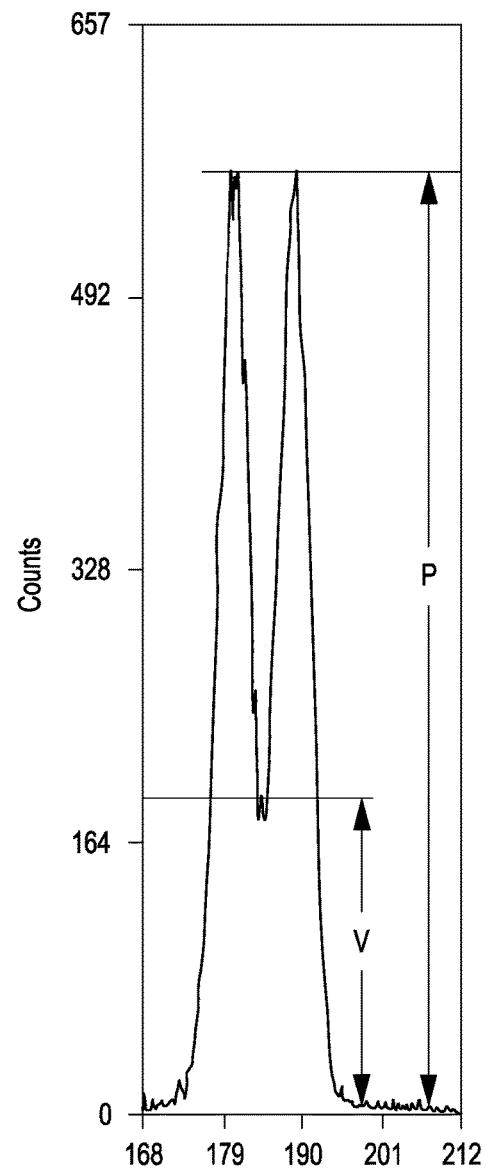
FIG. 4 illustrates a graphical representation of various sort parameters acquired in a flow cytometer while sorting sperm according to various embodiments described herein.

FIG. 4 illustrates a univariate plot in the form of a histogram that may be produced by the analyzer (36) and generated into a graphical presentation for an operator. The data illustrated in FIG. 4 may represent the number of occurrence of peak signal intensities from the side or forward fluoresce within a certain period. In the case of sperm, X-chromosome bearing sperm and Y-chromosome bearing sperm tend to have peak intensities that vary by between 2 and 5%, depending on the species, and this difference is reflected in the bimodal distribution of peak intensities seen in FIG. 3. Because X-chromosome bearing sperm and Y-chromosome bearing sperm tend to have differing fluorescence values, each of the peaks represents either X-chromosome bearing sperm of Y-chromosome bearing sperm. Based on the sort logic applied within the analyzer (36), the population of cells in the histogram may be only those cells which were determined to be viable oriented cells, such as those falling into R1 in FIG. 3, or they may represent cells which were not determined to be dead or undesirable, such as every event except those falling in R2. A variety of sorting parameters may be derived from the information contained within this histogram. For example, the level of distinctiveness between the two peaks may provide an indication of what a sorted purity may look like. FIG. 4 further illustrates relative intensity measurements at the lowest point between the two groups, which may be considered a value V and a second relative intensity at the peak or peaks of the histogram at P. A visual inspection of a histogram may provide an operator with an idea of how a flow cytometer is performing, but previously written computer instructions for determining a P value, a V value, and a ratio of V to P has not been implemented in flow cytometers. The valley to peak ratio, may be determined as a measured sorting parameter periodically during the course of sorting. The valley to peak ratio, while not the necessarily completely determinative of sorting purities, may provide a means for quickly estimating purity values, either by the execution of written instruction in the analyzer (36), or by visual inspection by an operator. Alternatively, the peak to valley ratio may provide a value which may be utilized in a similar manner.

Figure 5:
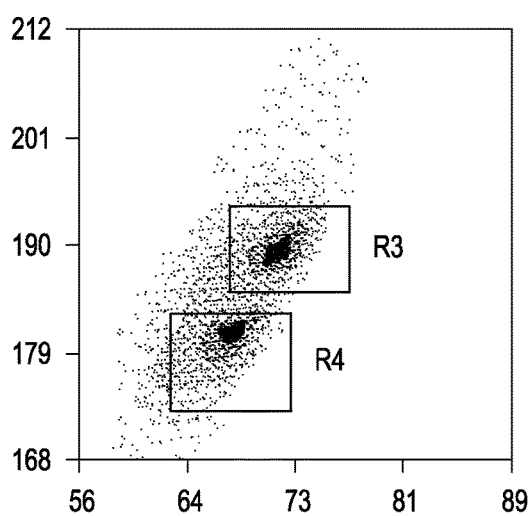
FIG. 5 illustrates a graphical representation of various sort parameters acquired in a flow cytometer while sorting sperm according to various embodiments described herein.

Turning to FIG. 5, a second bimodal plot may be generated by the analyzer (36) in response to signals acquired by the cell sensing system (30). The bimodal plot may represent a first axis illustrating the peak intensity value of a forward fluorescence signal or the peak intensity of side fluorescence signal. Like FIG. 4, the data illustrated in FIG. 5 may be gated such that only events falling within R1 in FIG. 3 are included. Alternatively, in the case of sperm, all events which do not fall into the dead gate R2 may also be displayed.

R3 may represent an X-sort gate for collecting X-chromosome bearing sperm. The term X-sort gate may be used interchangeably herein with the term X-gate. With reference to FIG. 5, it may demonstrate how changing the dimensions of the gating regions may affect efficiency, purity, and productivity. If the R3 region were to be expanded, it could be seen that every second more sperm would be sorted as X-chromosome bearing sperm resulting in higher sorting efficiency and higher productivity. However, the expansion of the R3 gate or region would begin to include events having an increasing likelihood of being Y-chromosomes bearing sperm. In order to increase the sorted purity of sperm, the R3 region can be made smaller and/or moved away from the Y-chromosome region. As fewer events fall within the X-sort gate, fewer sperm are sorted in the X-chromosome bearing sperm population and those which are have a greater probability of actually being X-chromosome bearing sperm, meaning the collected purity may be increased. However, both the efficiency, in terms of cells collected, and the productivity, in terms of sorts per second, will decrease as fewer events fall within the R3 region. Additionally, as other instrument parameters are modified, the illustrated graphs of FIG. 3, FIG. 4, and FIG. 5 may change in shape and nature. For example, increasing a sample pressure or a sample flow rate may result in a reduction in the valley to peak ratio, or may otherwise lessen the bimodal distinction between X-chromosome bearing sperm and Y-chromosome bearing sperm.

Figure 6:
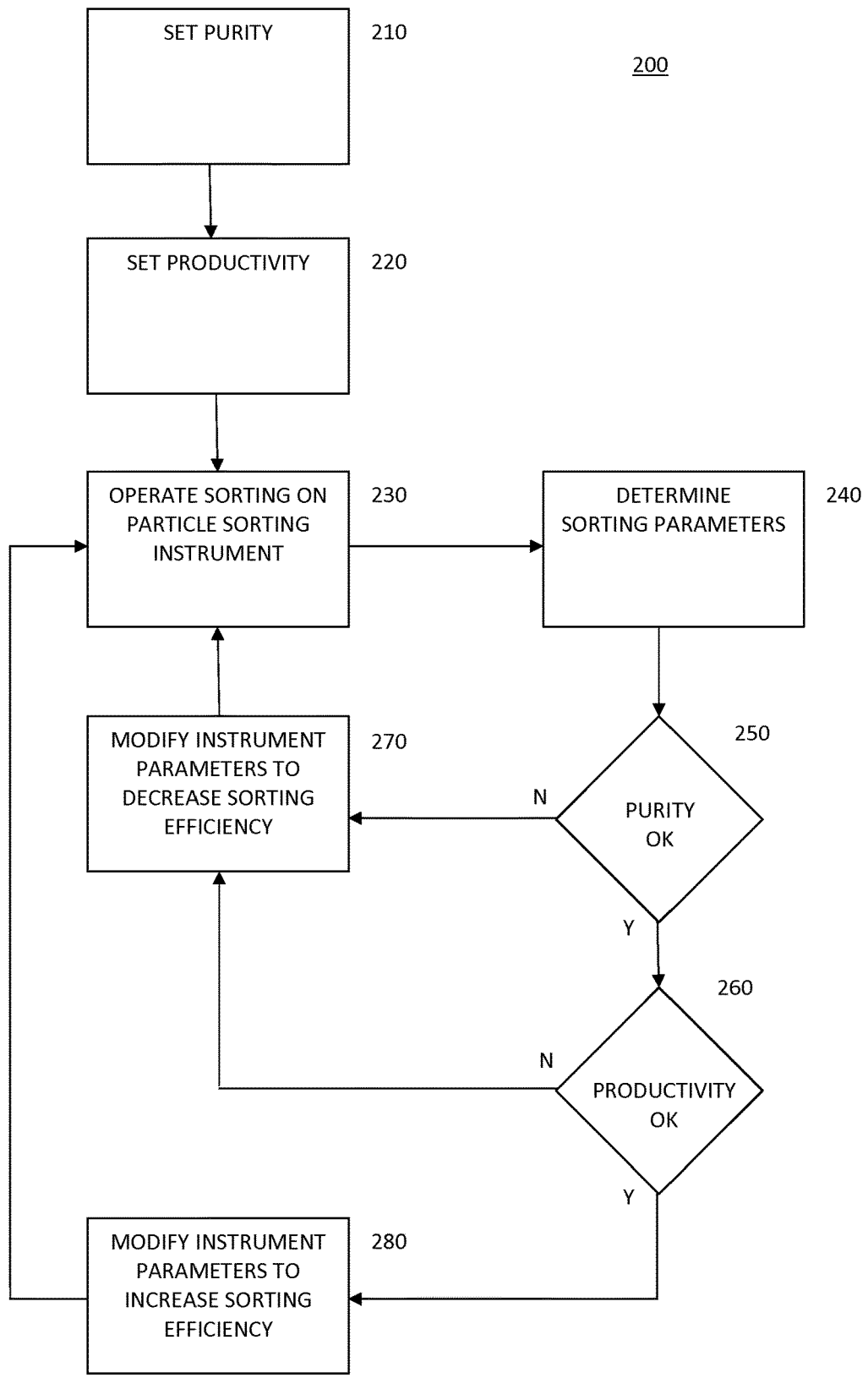
FIG. 6 illustrates a flow chart of a method in accordance with certain embodiments described herein.

Turning to FIG. 6, a method (200) of efficiently sorting sperm is illustrated in the form of a flow chart. The method may begin with the step of setting a purity (210), which may be a minimum threshold purity. The minimum purity threshold may be set by an operator based on an expected performance of a particle sorting instrument as well as based on the expected performance of a particular ejaculate, or a particular animal. Alternatively, a minimum purity threshold may be established after a sample has been partially analyzed or sorted. The minimum purity threshold may be entered into the analyzer (36) for comparison against various measured sorting parameters, or may be maintained by an operator, for making manual adjustment to the particle sorting device based on measured sorting parameters. The minimum purity threshold may be may be set at about 86%, at about 87%, at about 88%, at about 89%, at about 90%, at about 91%, at about 92%, at about 93%, at about 94%, at about 95%, at about 96%, at about 97%, at about 98%, or at about 99%.

The productivity may be set (220) before the purity is set, after the purity is set, or at the same time. The productivity may be determined in terms of sorts per second and may be set as a minimum productivity threshold. It should be appreciated that sperm samples which are stained in a manner that reduces the number of dead sperm and are sorted at increased concentrations may be sorted at particularly high productivities. Further increases in productivity may be achieved by expanding sort regions and reducing the minimum purity threshold.

The minimum productivity threshold may be set at about 3,000 sorts per second, 3,500 sorts per second, about 4,000 sorts per second, about 4,500 sorts per second, about 5,000 sorts per second, about 5,500 sorts per second, about 6,000 sorts per second, about 6,500 sorts per second, about 7,000 sorts per second, about 7,500 sorts per second, about 8,000 sorts per second, about 8,500 sorts per second, about 9,000 sorts per second, about 9,500 sorts per second, about 10,000 sorts per second, about 10,500 sorts per second, about 11,000 sorts per second, about 11,500 sorts per second, about 12,000 sorts per second, about 12,500 sorts per second, about 13,000 sorts per second, about 13,500 sorts per second, or about 14,000 sorts per second.

Once each of the purity and the productivity minimum thresholds are set, a particle sorting instrument may begin, or continue the operation of analyzing and sorting particles (230). In the course of operation sorting parameters may be determined (240). The sorting parameters may include those conditions relating to sorting preformed in a particle sorting instrument. Sorting parameters may include measured sorting parameters, parameters which are determined offline, parameters estimated by an operator, and conditions relating to a sorted population of particles or cells. Measured sorting parameters may be determined in the analyzer (36) and can include those conditions relating to sorting measured directly, calculated, or determined in a particle sorting instrument while analyzing and/or sorting a population of particles or cells, such as the event rate, sort rate, sorting efficiency, abort rate, dead gate percentage, live oriented gate percentage, valley to peak ratio, or the percentage of events in other sorting gates, such as an X-sort gate or a Y-sort gate.

A purity for comparison to the minimum purity threshold may be estimated by an operator based on the graphical representations generated by the analyzer, such as illustrated in FIG. 3, FIG. 4, and FIG. 5. A purity may also be determined offline, such as in a subsequent purity analysis of sperm nuclei. The purity may also be estimated with the execution of written instructions in the analyzer (36). The analyzer (36) may evaluate measured sorting parameters, such as the valley to peak ratio to estimate the purity. An algorithm for estimating purity may incorporate empirical data based on previous valley to peak ratios coordinated with purities subsequently determined offline from sonicated sperm (tailless sperm or sperm nuclei).

The productivity determined in the analyzer (36) may be compared from the measured sorting parameters directly against the minimum productivity threshold (260). In the event both the purity and productivity, however determined, are above their respective minimum threshold values, one or more instrument parameters may be adjusted to increase sorting efficiency (280). The instrument parameters may be adjusted manually by an operator, or the analyzer may execute written instructions automatically for varying the sample pressure, the sample flow rate, or one or more sorting regions. As one example, where purities are determined to be well over the minimum purity threshold.

As one example, the sort logic may be adjusted. The sort logic may be considered the logic applied by the analyzer (36) to determine which cells are sorted and which are discarded with waste. The sort logic may include an abort logic which determines when coincident events will be aborted in the course of sorting. For example, when a high purity is desired, every coincident event may be aborted, whereas when high productivity is desired an abort logic which accepts coincident events may be applied. Depending on the frequency and accuracy with which purity is determined, a percentage of coincident events may also be accepted.

As another example, sorting gates or sorting regions may be modified. When both the purity and the productivity are above their respective thresholds, sorting gates, such as the live gate illustrated in FIG. 3 as R1 may be enlarged to include more events. Similarly, the X-sort gate illustrated in FIG. 5 as R3, the Y-sort gate illustrated in FIG. 5 as R4, or both may be enlarged to sort more particles.

In one embodiment, a change to the drop drive frequency may reduce the number of coincident events by producing more droplets in a given time period and with fewer droplets having more than one cell. Similarly the drop drive amplitude may be modified.

In one embodiment, the sample flow rate may be modified when the minimum purity threshold and minimum productivity are met. In order to increase sort efficiency the sample pressure, or correspondingly the sample flow rate, may be reduced. Such a reduction in sample flow rate increases efficiency by reducing the number of coincident events and improving cell alignment and orientation. Accordingly, in order to further improve efficiency, the sort regions may be expanded while reducing the sample pressure or sample flow rate.

The fluid flow rate in combination with the concentration of cells in the sample together directly affect the measured parameter of the event rate. The measured parameter of the event rate may then be targeted to improve sorting efficiency. The event rate may be targeted between 2,000 and 20,000 events per second at standard concentrations of sperm, such as a sperm sample between 75 and 100 million sperm per ml. At high concentrations of sperm, such as 150 million sperm per ml and greater, event rates may be targeted between 2,000 events per second and 35,000 events per second, or higher.

In the event either the purity and productivity, however determined, are below their respective minimum threshold values, one or more instrument parameters may be adjusted to decrease sorting efficiency, or to increase either the purity or productivity (270). The instrument parameters may be adjusted manually by an operator, or the analyzer may execute written instructions automatically for varying the sample pressure, the sample flow rate, or one or more sorting regions.

As an exemplary embodiment, when the productivity minimum threshold is exceeded, but the purity minimum threshold is not, the sample flow rate may be reduced, or one or more of the live oriented sort region (R1) or the X-sort gate (R3) or Y-sort gate (R4) may be decreased to include fewer events, including those events which tend to be outside the required purity. Similarly, in the event the abort logic had been operating in a coincidence accept mode, it may be switched to a coincided reject mode, or to a mode which rejects an increased percentage of coincident events. In the event the minimum purity threshold is met, but the minimum production threshold is not, one or more sort regions may be increased in size to include more events.

After any modifications, the particle sorting instrument may continue to operate and sorting parameters may continue to be determined Adjustments may then proceed to incrementally improve or maximize the sorting efficiency. Optionally, the incremental adjustments towards a maximum sorting efficiency may stop once either the purity or the productivity approaches a predetermined margin of their respective minimum thresholds.

Figure 7:
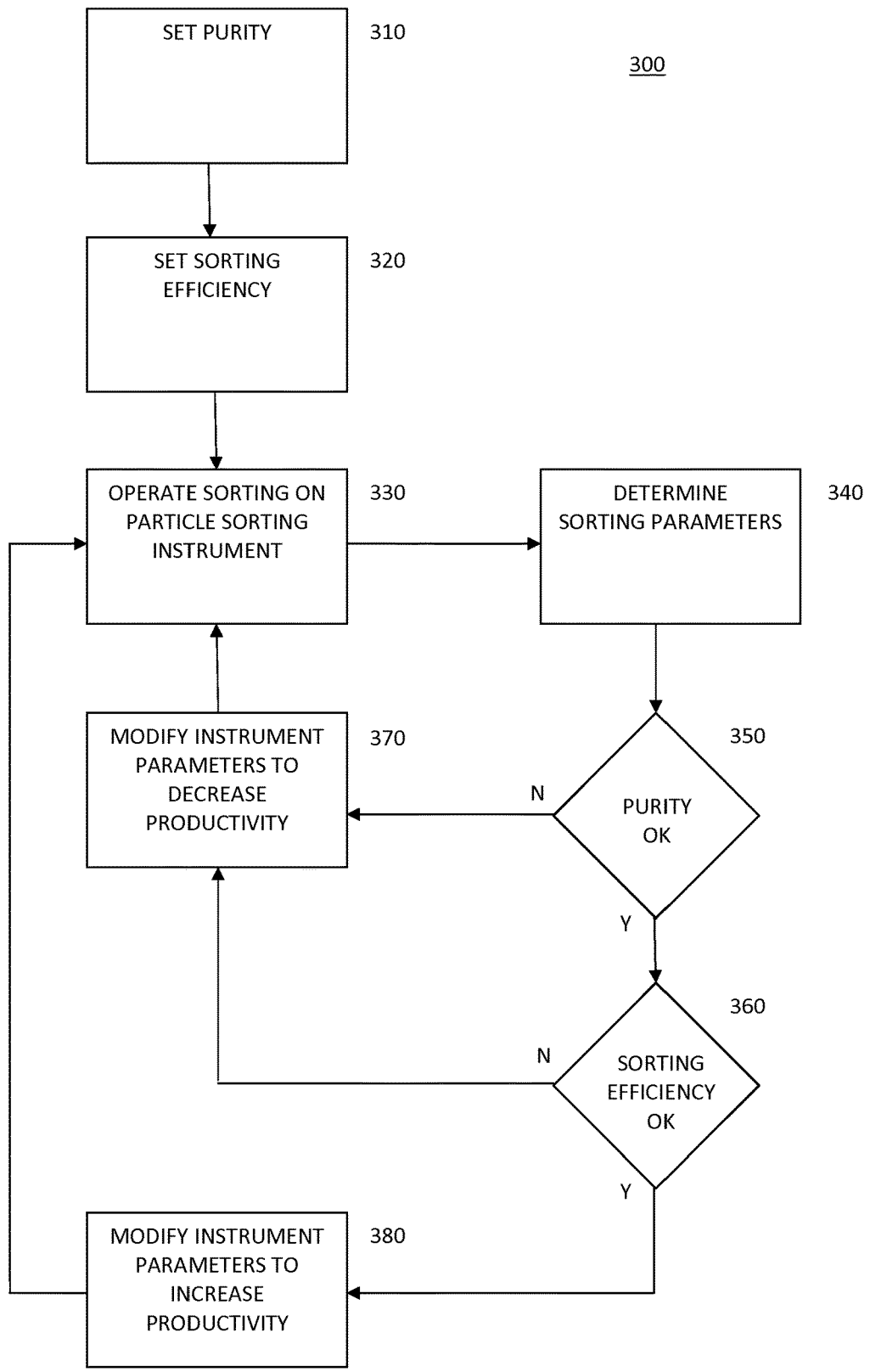
FIG. 7 illustrates a flow chart of a method in accordance with certain embodiments described herein.

Referring to FIG. 7, a method (300) of efficiently sorting sperm, while maximizing productivity is illustrated in the form of a flow chart. The method may begin with the step of setting a purity (310), which may be a minimum threshold purity. The minimum purity threshold may be set by an operator based on an expected performance of a particle sorting instrument as well as based on the expected performance of a particular ejaculate, or even a particular animal. Alternatively, a minimum purity threshold may be established after a sample has been partially analyzed or sorted. The minimum purity threshold may be entered into the analyzer for comparison against various measured sorting parameters, or may be maintained by an operator, for making manual adjustment to the particle sorting device based on measured sorting parameters. The minimum purity threshold may be set at about 86%, at about 87%, at about 88%, at about 89%, at about 90%, at about 91%, at about 92%, at about 93%, at about 94%, at about 95%, at about 96%, at about 97%, at about 98% or at about 99%.

A sorting efficiency may be set (320) before the purity is set, after the purity is set, or at the same time. The sorting efficiency may be determined in terms of the percentage of sperm cells sorted or collected over a period of time relative to the total population of sperm cells analyzed during that period of time. The sorting efficiency may also be determined in terms of a yield on live cells. For example, the sorting efficiency may be determined as the percentage of cells sorted or collected over a period of time relative to the population of cells not considered to be dead or non-viable (i.e. every cell outside the R2 region seen in FIG. 3).

Once each of the purity and the sorting efficiency minimum thresholds are set a particle sorting instrument may begin, or continue, the operation (330) of analyzing and sorting particles. In the course of operation sorting parameters may be determined (340). The sorting parameters may include those conditions relating to sorting preformed in a particle sorting instrument. Sorting parameters may include measured sorting parameters in addition to parameters which are determined offline, estimated by an operator, and conditions relating to a sorted population of particles or cells. Measured sorting parameters may be determined in the analyzer (36) and can include those conditions relating to sorting measured directly, calculated or determined in a particle sorting instrument while analyzing and/or sorting a population of particles or cells, such as the event rate, sort rate, sorting efficiency, abort rate, dead gate percentage, live oriented gate percentage, valley to peak ratio, or the percentage of events in other sorting gates, such as an X-sort gate or a Y-sort gate.

A purity for comparison to the minimum purity threshold (350) may be estimated by an operator based on the graphical representations generated by the analyzer, such as illustrated in FIG. 3, FIG. 4, and FIG. 5. A purity may also be determined offline, such as in a subsequent purity analysis of sperm nuclei. The purity may also be estimated with the execution of written instructions in the analyzer (36). The analyzer (36) may evaluate measured sorting parameters, such as the valley to peak ratio to estimate the purity. An algorithm for estimating purity may be developed from empirical data based on previous valley to peak ratios coordinated with purities subsequently determined offline from sonicated sperm (e.g. tailless sperm or sperm nuclei).

The sorting efficiency determined in the analyzer (36) may be compared from the measured sorting parameters directly against the minimum sorting efficiency threshold (360). In the event both the purity and sorting efficiency, however determined, are above their respective minimum threshold values, one or more instrument parameters may be adjusted to increase productivity (380). The instrument parameters may be adjusted manually by an operator, or the analyzer may execute written instructions automatically for varying the sample pressure, the sample flow rate, or one or more sorting regions.

As one example, the sort logic may be adjusted to increase productivity. The sort logic may be considered the logic applied by the analyzer (36) to determine which cells are sorted and which are discarded with waste. The sort logic may include an abort logic which determines when coincident events will be aborted in the course of sorting. For example, when a high purity is desired, every coincident event may be aborted, whereas when high sorting productivity is desired an abort logic which accepts coincident events may be applied. Alternatively, a percentage of coincident events may also be accepted.

As another example, sorting gates or sorting regions may be modified. When both the purity and the sorting efficiency are above their respective thresholds, sorting gates, such as the live gate illustrated in FIG. 3 as R1 may be enlarged to include more events in order to increase productivity. Similarly, the X-sort gate illustrated in FIG. 5 as R3, the Y-sort gate illustrated in FIG. 5 as R4, or both may be enlarged to sort more particles.

In one embodiment, a change to the drop drive frequency may reduce the number of coincident events by producing more droplets in a given time period and with fewer droplets having more than one cell. Similarly the drop drive amplitude may be modified.

In one embodiment, the sample flow rate may be modified when the minimum purity threshold and minimum sorting efficiency thresholds are met. In order to increase productivity the sample pressure, or correspondingly the sample flow rate, may be increased. Such an increase in sample flow rate increases the number of events per unit time, possibly at a cost to efficiency and a slight cost to purity. In order to further improve productivity and sort efficiency, albeit at a cost to purity, the sort regions may be expanded while increasing the sample pressure, or sample flow rate.

The fluid flow rate in combination with the concentration of cells in the sample directly affect the measured parameter of the event rate. The measured parameter of the event rate, may then be targeted to improve sorting efficiency while maximizing productivity. The event rate may be targeted between 2,000 and 20,000 events per second at standard concentrations of sperm, such as sperm sample between 75 and 100 million sperm per ml. At high concentrations of sperm, such as 150 million sperm per ml and greater, event rates may be targeted between 2,000 events per second and 35,000 events per second, and higher.

In the event either the purity and sorting efficiency, however determined, are below their respective minimum threshold values, one or more instrument parameters may be adjusted to decrease productivity, or to increase either the purity or sorting efficiency (370). The instrument parameters may be adjusted manually by an operator, or the analyzer may execute written instructions automatically for varying the sample pressure, the sample flow rate, or one or more sorting regions.

As an exemplary embodiment, when the sorting efficiency minimum threshold is exceeded, but the purity minimum threshold is not, the sample flow rate may be reduced, or one or more of the live oriented sort region (R1) or the X-sort gate (R3) or Y-sort gate (R4) may be decreased in size or shifted to include fewer events, effectively excluding more events which tend to be outside the required purity. Similarly, in the event the abort logic had been operating in a coincidence accept mode, it may be switched to a coincided reject mode, or to a mode which rejects an increased percentage of coincident events. In the event the minimum purity threshold is met, but the minimum sorting efficiency threshold is not, one or more sort regions may be increased in size or shifted to include more events, including more events which are less likely to meet the purity threshold.

After any modifications, the particle sorting instrument may continue to operate and sorting parameters may continue to be determined Adjustments may then proceed to incrementally improve or maximize the productivity. Optionally, the incremental adjustments towards a maximum productivity may stop once either the purity or the sorting efficiency approaches a predetermined margin of their respective minimum thresholds.

Various modifications to the method described in FIG. 6 and FIG. 7 may be implemented in order to accommodate different animals. In the case of bovine, a young genomic sire may have a lower sperm count as compared to more mature animals. The minimum purity threshold and/or productivity threshold may be adjusted accordingly to achieve an efficient use of sperm.

Example 1—Standardizing Sperm Samples and One Step Staining

Collection—
Sperm was collected from five different bulls on a routine collection schedule using an artificial vagina. Each bull was collected two or three times in one day. Of the five bulls, two were Jersey bulls and three were Holstein bulls. All ejaculates contained greater than 60% progressive motility and sperm concentration varied from 857 million sperm per mL to 2480 million sperm per mL. Ejaculates collected from the same bull were pooled then divided into nine sperm samples for collection and staining treatments.

Staining—
Portions of each bull ejaculate were stained with nine different methods.

(A) Control (no standardization, two step staining)—A control was established which did not include the step of standardizing collected ejaculates and in which the sperm was stained in two steps. Prior to staining, the sperm samples were concentrated to between 1700 million sperm per mL and 1800 million sperm per mL by centrifugation or by the addition of a tris-egg yolk buffer having a pH of 6.8, depending on the samples starting concentration.

Sperm in the control group was diluted to $160 \times 10^6$ sperm per ml in a modified TALP buffer, as described in Table 1, at a pH of 7.4. Each sperm sample in the control group was then incubated with 16-17 µM of Hoechst 33342 per ml (64-68 µM) of sample for 45 minutes at 34° C. After incubation, an equal volume of a second modified TALP was added reducing the concentration to $80 \times 10^6$ sperm per mL. The second modified TALP includes the components described in Table 1 with the addition of 4% egg yolk, 50 µM yellow food dye No. 6 (20 g/L) and the pH was dropped to 5.5 with the addition of HCl.

(B) Extended (no standardization, two step staining)—In the second group, sperm was not standardized, but was extended with a buffer and 20% egg yolk. The sperm was then concentrated to between 1700 million sperm per mL and 1800 million sperm per mL in the same manner described with respect to group (A). The sperm was then diluted to $160 \times 10^6$ sperm per ml in a modified TALP buffer, and stained in the same two step manner described in group (A).

(C) One Step I (no standardization, one step staining with 1% egg yolk)—In a third group sperm was collected and the concentration was adjusted in the same manner as the control group (A). Each sperm sample was then diluted to $160 \times 10^6$ sperm per ml in a modified TALP buffer at a pH of 7.4. The modified TALP buffer was substantially identical to the buffer described in Table 1, except that it additionally included 1% egg yolk and yellow food dye No. 6 at a concentration of 25 µM. Each sperm sample in this group was then incubated with 14-15 µM of Hoechst 33342 per ml (56-60 µM) for 45 minutes at 34° C. After incubation, sperm remained at a concentration of $160 \times 10^6$ sperm per ml.

(D) Standardized I (standardized with 3% egg yolk buffer, two step staining)—In this group sperm was standardized by adjusting both the pH and sperm concentration prior to staining and sorting. After collection sperm was diluted 1:3 in an initial buffer having a pH of 7.2 as well as a high capacity for buffering pH. The high capacity buffer was supplemented with 3% egg yolk. All samples were then centrifuged to bring the sperm concentration down to between 1700 million sperm and 1800 million sperm per mL. The standardized sperm was then stained according to the two step method described in (A).

(E) Standardized II (standardized with 10% egg yolk buffer, two step staining)—In this group sperm was standardized by adjusting both the pH and sperm concentration prior to staining in the same manner described in group (D), except that the initial buffer was 10% egg yolk.

(F) One Step and Standardized I (standardized with 3% egg yolk buffer, one step staining with 1% egg yolk)—In this group sperm was standardized by adjusting both the pH and sperm concentration prior to sorting in the same manner described in group (D). The standardized sample was then stained with a one step staining process as described in group (C).

(G) One Step and Standardized II (standardized with 10% egg yolk buffer, one step staining with 1% egg yolk)—In this group sperm was standardized by adjusting both the pH and sperm concentration prior to staining in the same manner described in group (E). The standardized sample was then stained with a one step staining process as described in group (C).

(H) One Step and Standardized III (standardized with 3% egg yolk buffer, one step staining with no egg yolk)—In this group sperm was standardized by adjusting both the pH and sperm concentration prior to staining in the same manner described in group (D). The standardized sample was then stained with a one step staining process as described in group (C), except that no egg yolk was added to the one step staining TALP.

(I) One Step and Standardized IV (standardized with 10% egg yolk buffer, one step staining with no egg yolk)—In this group sperm was standardized by adjusting both the pH and sperm concentration prior to sorting in the same manner described in group (E). The standardized sample was then stained with a one step staining process as described in group (C) except that no egg yolk was added to the one step staining TALP.

Sorting and Data Acquisition—

Each of the stained samples was sorted on a MoFlo SX (Beckman Coulter, USA). Those samples which were stained in a two step process were sorted at the concentration of $80 \times 10^6$ sperm per mL, and those samples which were stained by the one step process were sorted at the concentration of $160 \times 10^6$ sperm per mL. Data logged by the flow cytometer was recorder including information relating to the sort rates and gating of sperm subpopulations. For example, the percentage of sperm gated as dead, as well as the percentages of sperm gated as live-oriented and over ranges were recorded and averaged for the five bulls.

Results—

A comparison of the percentage of sperm which was orientated, unoriented and dead as determined by the sort parameters established in the flow cytometer are summarized in Table 2 below.

TABLE 2

| | % Oriented | % Non-oriented | % Dead | Sort Rate | Over-range |
|---|---|---|---|---|---|
| A) Control | 58.29% | 18.02% | 16.89% | 3500 | 4.32% |
| B) Extended | 60.54% | 20.20% | 8.71% | 3400 | 10.36% |
| C) One Step I | 61.04% | 17.96% | 12.31% | 3500 | 5.65% |
| D) Standardized I | 52.78% | 18.14% | 9.71% | 2900 | 24.73% |
| E) Standardized II | 55.20% | 18.70% | 6.04% | 3200 | 23.44% |
| F) One Step + Standardized I | 57.33% | 20.35% | 5.39% | 3200 | 16.17% |
| G) One Step + Standardized II | 59.99% | 18.89% | 5.19% | 3600 | 16.83% |
| H) One Step + Standardized III | 62.67% | 22.02% | 6.97% | 3800 | 6.23% |
| I) One Step + Standardized IV | 63.49% | 23.16% | 5.61% | 4100 | 5.38% |

As compared to the control (A), the groups One Step I (C), Standardized I (D), and Standardized II (E), each exhibited significantly lower dead populations with reductions of 4.58%, 7.18% and 10.85%, respectively. Based on these improvements, the steps of standardizing sperm samples before staining and modifying the staining process to a single step independently improve the ability of sperm to survive the sorting process. Additionally, One Step and Standardized I (F), One Step and Standardized II (G), One Step and Standardized III (H), and One Step and Standardized IV (I), demonstrate a synergy whereby the combined effect of standardizing an ejaculate and staining the ejaculate in a single step is greater than either improvement individually.

Referring to Table 2, it can be seen that Standardize 1 (D), Standardize II (E), One Step and Standardized I (F), and One Step and Standardized II (G), each appeared to provide significant benefits in terms reducing the number of dead sperm, but the percentage of oriented sperm did not improve. This may be related to the column indicated as over range. While more sperm were gated as live for sorting there appears to be an increase in signals scattered above the sorting gate ranges. This signal may represent sperm which is stuck together or may represent sperm which is bound to egg yolk lipids. In either event, the general pattern emerges that greater quantities of egg yolk reduce dead sperm numbers, but may introduce a new issue and a balance may therefore be required.

Example 2—Standardizing Sperm Samples and One Step Staining

Collection—

Sperm was collected from six different Jersey bulls on a routine collection schedule using an artificial vagina. All ejaculates contained greater than 65% progressive motility and sperm concentration varied from 765 million sperm per mL to 1710 million sperm per mL. Each Sperm sample was divided into two parts in 15 mL tubes for two collection and staining treatments. pH measurements were taken at collection, and at each subsequent processing step.

Staining—

Control (no standardization, two step staining)—A control was established which did not include the step of standardizing collected ejaculates and in which the sperm was stained in two steps. Prior to staining, the sperm samples were concentrated to between 1700 million sperm per mL and 1800 million sperm per mL by centrifugation or by the addition of a tris-egg yolk buffer having a pH of 6.8, depending on the samples starting concentration.

Sperm in the control group was diluted to $160 \times 10^6$ sperm per ml in a modified TALP buffer, as described in Table 1, at a pH of 7.4. Each sperm sample in the control group was then incubated with 16-17 μM of Hoechst 33342 per ml (64-68 μM) of sample for 45 minutes at 34° C. After incubation, an equal volume of a second modified TALP was added reducing the concentration to $80 \times 10^6$ sperm per mL. The second modified TALP includes the components described in Table 1 with the addition of 4% egg yolk, 50 μM red food dye No. 40 (20 g/L) and the pH was dropped to 5.5 with the addition of HCl.

One Step and Standardized (standardized with 10% egg yolk, one step staining with one percent egg yolk)—Sperm was standardized by adjusting both the pH and sperm concentration prior to staining. After collection sperm was diluted 1:3 in an initial buffer having a pH of 7.2 as well as a high capacity for buffering pH. The high capacity buffer was supplemented with 3% egg yolk. All samples were then centrifuged to bring the sperm concentration down to between 1700 million sperm and 1800 million sperm per mL.

The sperm samples were then diluted to $160 \times 10^6$ sperm per ml in a modified TALP buffer at a pH of 7.4. The modified TALP buffer was substantially identical to the buffer described in Table 1, except that it additionally included 1% egg yolk and yellow food dye No. 6 at a concentration of 25 μM. Each sperm sample in this group was then incubated with 16-17 μM of Hoechst 33342 per ml (64-68 μM) for 45 minutes at 34° C. After incubation, sperm remained at a concentration of $160 \times 10^6$ sperm per ml.

Sorting and Data Acquisition—

Each sample was sorted on a MoFlo SX (Beckman Coulter, USA). The control was sorted at the concentration of $80 \times 10^6$ sperm per mL, while the standardized sperm was sorted at $160 \times 10^6$ sperm per mL. Data was logged by the flow cytometer and then averaged for the 6 bulls.

Results—

FIG. 3 illustrates the recorded pH of both the control (A) and the standardized ejaculate (B). These Values are reflected in TABLE 3 below. While the standardized ejaculate is subject to an initial increase, a subsequent increase is avoided during staining and the following drop off is also avoided. Additionally, TABLE 4 illustrates similar benefits in the reduction of dead sperm that was seen in Example 1. Specifically, the standardized sample which was stained in one step had 5.67% less dead sperm.

izing collected ejaculates and in which the sperm was stained in two steps. Sperm in the control group was diluted to $160 \times 10^6$ sperm per ml in a modified TALP buffer, as described in Table 1, at a pH of 7.4. Each sperm sample in the control group was then incubated with 16-17 μM of Hoechst 33342 per ml (64-68 μM) of sample for 45 minutes at 34° C. After incubation, an equal volume of a second modified TALP was added reducing the concentration to $80 \times 10^6$ sperm per mL. The second modified TALP includes the components described in Table 1 with the addition of 4% egg yolk, 50 μM red food dye No. 40 (20 g/L) and the pH was dropped to 5.5 with the addition of HCl.

Standardized III and One Step (standardized with 3% egg yolk buffer, one step staining)—The remaining sperm was standardized by adjusting both the pH and sperm concentration prior to staining and sorting. After collection sperm was diluted 1:3 in an initial buffer having a pH of 7.2 as well as a high capacity for buffering pH. The high capacity buffer was supplemented with 3% egg yolk. The sperm sample was then diluted to $160 \times 10^6$ sperm per ml in a modified TALP buffer at a pH of 7.4. The modified TALP buffer was substantially identical to the buffer described in Table 1, except that it additionally included 1% egg yolk and yellow food dye No. 6 at a concentration of 25 μM. Each sperm sample in this group was then incubated with 14-15 μM of Hoechst 33342 per ml (56-60 μM) for 45 minutes at 34° C. After incubation, sperm remained at a concentration of $160 \times 10^6$ sperm per ml.

The control group was run through a Legacy MoFlo SX (Beckman Coulter, Miami Fla., US) with a digital upgrade at a concentration of $80 \times 10^6$ sperm per ml, while the Standardized III and One Step was sorted at a concentration of $160 \times 10^6$ sperm per ml. Table 5 illustrates the percentage of cells in the dead gate of each ejaculate and the average. After sorting, percentages of sperm occurring in the dead gates (R2 seen in FIG. 3), were indicated for both samples.

TABLE 3

|  | Initial | Before Centrifugation | After Centrifugation | During Staining | After staining | Before cytometer |
|---|---|---|---|---|---|---|
| Control (A) | 6.34 | 6.34 | 6.25 | 7.22 | 7.07 | 6.59 |
| Standardized (B) | 6.34 | 7.12 | 6.85 | 7.18 | 6.98 | 6.98 |

TABLE 4

|  | PV | % Oriented | % Dead | Sort Rate | Duplets/ Triplets |
|---|---|---|---|---|---|
| Control | 1.86 | 52.99 | 14.63 | 35.83 | 21.73 |
| Standardized – One Step | 1.97 | 57.22 | 8.96 | 37.00 | 24.59 |
| Difference | 0.11 | 4.23 | −5.67 | 1.17 | 2.86 |

Example 3—Standardizing Sperm Samples and One Step Staining Reduces Dead Sperm Collection—

Sperm was collected from three different Jersey bulls and three different Holstein bulls on a routine collection schedule for a total of 17 collections. Each ejaculate was divided for two treatments.

Staining—

Control (no standardization, two step staining)—A control was established which did not include the step of standard-

TABLE 5

| | Bull | Dead Gate (%) | |
|---|---|---|---|
| Ejaculate Number | Bull | CONTROL | ONE-STEP and STANDARDIZED III |
| 01 | Holstein Bull 1 | 16% | 12% |
| 02 | Holstein Bull 2 | 26% | 6% |
| 03 | Jersey Bull 1 | 15% | 7% |
| 04 | Holstein Bull 2 | 19% | 3% |
| 05 | Jersey Bull 1 | 13% | 6% |
| 06 | Holstein Bull 3 | 19% | 12% |
| 07 | Jersey Bull 2 | 25% | 14% |
| 08 | Holstein Bull 1 | 25% | 21% |
| 09 | Holstein Bull 2 | 20% | 20% |
| 10 | Jersey Bull 3 | 9% | 5% |
| 11 | Jersey Bull 2 | 19% | 17% |
| 12 | Holstein Bull 3 | 15% | 14% |
| 13 | Jersey Bull 1 | 10% | 7% |
| 14 | Holstein Bull 1 | 9% | 6% |
| 15 | Holstein Bull 1 | 9% | 8% |
| 16 | Holstein Bull 3 | 17% | 6% |

TABLE 5-continued

| | Bull | Dead Gate (%) | |
| --- | --- | --- | --- |
| Ejaculate Number | Bull | CONTROL | ONE-STEP and STANDARDIZED III |
| 17 | Holstein Bull 3 | 16% | 5% |
| | Average | 17% | 10% |

Example 4—Optimizing Sorting Efficiency in Flow Cytometer

Sperm was collected from a Holstein bull and stained according to the Standardized III and One step protocol described in the previous examples. The sample was placed on Legacy MoFlo SX (Beckman Coulter, Miami Fla., US) with a digital upgrade. During sorting, sheath fluid pressure was established at 40 PSI and the drop drive frequency was set to 64.9 KHz. The sample pressure was adjusted to target event rates of about 1500, 3500, 7500, 8500, 10,000 15000, 20000, 25000, and 30000.

The ejaculate in this example demonstrated about a 3%-5% dead gate which allowing for large portions of the sperm to be included in the live oriented gate; between 79.1% and 85.4%. The sorting logic utilized in this sort gated on a live oriented region of sperm (R1). R1 was established by an operator to retain a large portion of sperm. The X-sort gate was similarly established by an operator with a target of 90% purity. Data was periodically digitally logged for several samples at each event rate. Data was averaged at each event rate to provide averages for productivity (Sort Rate), sorting efficiency (Sort Rate/Event Rate), Valley to Peak ratio, abort rate, as well as the percentage of the population in the Dead gate (R2), the percentage of the population in the live oriented gate (R1), the percentage of the population of sperm in the X-Sort gate (R3), and the percentage of viable (live) sperm in the X-Sort Gate. Additionally, purities were determined off line for each sperm sorted at each event rate setting. Purities were determined by sonicating the tails off 1 million sperm and collected at each group of event rates and measurement in an off line purity analyzer. This measurement was performed twice for each group and averaged.

sample was gated in the X-sort gate for event rates less than 10,000 events per second. The low percentage of dead sperm in combination with the high percentage of live oriented sperm allows gating an R3 region to be adjusted such that R3 encroaches the region of FIG. 5 where sperm cells have a greater probability to be Y-chromosomes bearing sperm than X-chromosome bearing sperm. Even when slightly encroaching this region, the purity checked post sort remained 96%, even though 54% of all sperm was included in the X-sort gate and 57% of all live sperm was included in the X-sort gate.

The synergistic combination of improved staining techniques in combination with sorting methods which focus on efficiency can be seen to provide reliable sperm sorting methods which may provide between 25% and about 40% yield on the total sperm population, and maintain purities greater than 90%.

Turning to FIG. 9, additional sort parameters are graphically illustrated from Table 6, including the purities for each group of event rates and the percentage of sperm cells in the live/oriented gate (R1) and the peak to valley ratio. Because, a purity of 90% was target by an operator the trends of the peak to valley ratio is not demonstrated in the measure purity but is reflected in the decreasing percentage of sperm in the X-Sort Gate.

One aspect of this disclosure projects more spatially efficient flow cytometers, which may allow more sorting heads in an available space. In such an arrangement, more flow cytometer sorting heads may be dedicated to a single sperm sample, and each one may be operated at an improved efficiency, thereby combining the benefits of efficient sorting methods with high productivity.

As can be easily understood from the foregoing, the basic concepts of the present invention may be embodied in a variety of ways. The invention involves numerous and varied embodiments of sex sorting sperm including, but not limited to, the best mode of the invention.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to

TABLE 6

| | Valley/ Peak (%) | Event Rate (Hz) | Sort Rate (Hz) | Sort Rate/ Event Rate (%) | Abort Rate (Hz) | Abort Rate/ Sort Rate | Dead Gate (%) | Live-Oriented (%) | X-Sort Gate (%) | X-Sort/ Viable (%) | X-Purity (%) |
| --- | --- | --- | --- | --- | --- | --- | --- | --- | --- | --- | --- |
| 1 | 67.4% | 1722 | 694 | 40.3% | 48 | 7.0% | 6.4% | 82.9% | 54.1% | 57.7% | 96.0% |
| 2 | 66.6% | 3697 | 1361 | 36.8% | 141 | 10.4% | 4.5% | 84.9% | 52.2% | 54.6% | 96.0% |
| 3 | 63.4% | 7377 | 2591 | 35.1% | 414 | 16.0% | 2.9% | 85.4% | 50.0% | 51.5% | 95.5% |
| 4 | 63.4% | 8515 | 3005 | 35.3% | 522 | 17.4% | 2.7% | 84.9% | 51.2% | 52.6% | 95.5% |
| 5 | 62.1% | 9891 | 3415 | 34.5% | 645 | 18.9% | 2.7% | 84.4% | 51.2% | 52.6% | 96.0% |
| 6 | 54.7% | 16686 | 4774 | 28.6% | 1306 | 27.4% | 2.8% | 82.8% | 47.1% | 48.5% | 93.0% |
| 7 | 51.0% | 19760 | 5080 | 25.7% | 1604 | 31.6% | 2.8% | 81.8% | 44.6% | 45.9% | 91.5% |
| 8 | 47.5% | 24839 | 5822 | 23.4% | 2175 | 37.4% | 2.8% | 80.2% | 43.5% | 44.8% | 90.0% |
| 9 | 43.9% | 29666 | 6332 | 21.3% | 2706 | 42.7% | 3.1% | 79.1% | 42.4% | 43.7% | 92.5% |

Turning to FIG. 8 a graphical representation of several measured sorting parameters is illustrated. In particular, it can be seen that low event rates reduce the abort rates and improve sorting efficiency. In particular, the abort rate is 7% of the sort rate when the event rate is 1722.

Additionally the synergistic effect of reducing dead sperm is illustrated by virtue of the fact over 50% of the sperm any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of "sorter" should be understood to encompass disclosure of the act of "sorting"—whether explicitly discussed or not—and, conversely, were there effectively disclosure of the act of "sorting", such a disclosure should be understood to encompass disclosure of a "sorter" and even a "means for sorting." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

Moreover, for the purposes of the present invention, the term "a" or "an" entity refers to one or more of that entity. As such, the terms "a" or "an", "one or more" and "at least one" can be used interchangeably herein.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

We claim:

1. A method of efficiently sorting a sperm sample in a particle sorting instrument comprising:
    establishing a sheath fluid stream in the particle sorting instrument;
    flowing a sperm sample into the sheath fluid stream;
    identifying viable X-chromosome bearing sperm and/or viable Y-chromosome bearing sperm in the sperm sample;
    separating the viable X-chromosome bearing sperm and/or the viable Y-chromosome bearing sperm from the remainder of the sperm sample;
    collecting the viable X-chromosome bearing sperm and/or the viable Y-chromosome bearing sperm;
    determining one or more measured sorting parameters in the particle sorting instrument including a sorting efficiency of analyzed sperm, wherein the sorting efficiency of analyzed sperm is calculated by continuously determining a ratio of a number of collected sperm to a number of events representing analyzed sperm over a period of time during sorting;
    establishing a minimum productivity threshold;
    establishing a minimum purity threshold;
    adjusting one or more instrument parameters to increase the sorting efficiency of analyzed sperm while maintaining the productivity, in terms of sorts per second, above the minimum productivity threshold and purity above the minimum purity threshold.

2. The method of claim 1, wherein additional measured sorting parameters are selected from the group consisting of: event rate, sort rate, valley to peak ratio, abort rate, percentage of particles in dead gate, percentage of particles in an X-sort gate, percentage of particles in a Y-sort gate, and percentage of particles in an oriented gate.

3. The method of claim 1, wherein the step of adjusting one or more instrument parameters comprises adjusting a sort logic.

4. The method of claim 3, wherein the step of adjusting the sort logic comprises accepting coincident events as long as the purity and the productivity remain above their minimum thresholds.

5. The method of claim 1, wherein the step of adjusting one or more instrument parameters comprises adjusting a sort gate.

6. The method of claim 5, wherein the step of adjusting a sort gate comprises the step of modifying a sort region for collecting X-chromosome bearing sperm and/or a sort region for collecting Y-chromosome bearing sperm to include more events representing analyzed sperm.

7. The method of claim 1, wherein particle sorting device comprises a jet-in-air flow cytometer and the step of adjusting one or more instrument parameters comprises adjusting a drop drive frequency.

8. The method of claim 1, wherein particle sorting device comprises a jet-in-air flow cytometer and the step of adjusting one or more instrument parameters comprises adjusting a drop drive amplitude.

9. The method of claim 1, wherein the step of adjusting the one or more instrument parameters comprises adjusting a sample flow rate.

10. The method of claim 9, wherein adjusting the sample flow rate controls an event rate in the particle sorting instrument.

11. The method of claim 10, wherein the event rate is adjusted to between about 2,000 events per second and about 20,000 events per second.

12. The method of claim 9, wherein the step of adjusting one or more instrument parameters is performed by an operator.

13. The method of claim 9, wherein the step of adjusting one or more instrument parameters is performed by a controller in response to a feedback provided with the particle sorting instrument.

14. The method of claim 1, wherein the step of adjusting one or more instrument parameters comprises reducing a sample flow rate or increasing a sort region.

15. The method of claim 1, wherein the particle sorting instrument sorts for only one of the X-chromosome bearing sperm and the Y-chromosome bearing sperm.

16. The method of claim 15, wherein the ratio of collected sperm to the total number of sperm in the population of sortable sperm is between about 25% and about 50%.

17. The method of claim 1, wherein the particle sorting instrument collects both the X-chromosome bearing sperm and the Y-chromosome bearing sperm separately.

18. The method of claim 1, wherein the minimum purity threshold is about 86%, about 87%, about 88%, about 89%, about 90%, about 91%, about 92%, about 93%, about 94%, about 95%, about 96%, about 97%, about 98% or about 99%.

19. The method of claim 1, wherein the minimum productivity threshold is set at about 3,000 sorts per second, 3,500 sorts per second, about 4,000 sorts per second, about 4,500 sorts per second, about 5,000 sorts per second, about 5,500 sorts per second, about 6,000 sorts per second, about 6,500 sorts per second, about 7,000 sorts per second, about 7,500 sorts per second, about 8,000 sorts per second, about 8,500 sorts per second, about 9,000 sorts per second, about 9,500 sorts per second, about 10,000 sorts per second, about 10,500 sorts per second, about 11,000 sorts per second, about 11,500 sorts per second, about 12,000 sorts per second, about 12,500 sorts per second, about 13,000 sorts per second, about 13,500 sorts per second, or about 14,000 sorts per second.

20. The method of claim 1, wherein where the step of adjusting one or more instrument parameters to increase the sorting efficiency of analyzed sperm while maintaining the productivity, in terms of sorts per second, above the minimum productivity threshold and purity above the minimum purity threshold further comprises the steps of estimating a purity and comparing the estimated purity to the minimum purity.

21. The method of claim 20, wherein the step of estimating purity further comprises the step of evaluating valley to peak ratios determined in the particle sorting instrument.

22. The method of claim 21, wherein the valley to peak ratios are compared to empirical data to predict a current purity.

23. The method of claim 22, wherein the step of comparing valley to peak ratios to empirical data is performed by the execution of written instructions stored in a processor associated with the particle sorting instrument.

24. The method of claim 1, which prior to the step of flowing a sperm sample into the sheath fluid stream further comprises the steps of:
 a) standardizing the concentration of the sperm sample;
 b) standardizing the pH of the sperm sample; and
 c) staining the sperm sample with a single staining solution having a DNA selective dye and a quenching dye to provide a stained sperm sample having a concentration of sperm between about $160 \times 10^6$ sperm cells per microliter and about $640 \times 10^6$ sperm cells per microliter.

25. The method of claim 1, further comprising the step of orienting sperm prior to the step of differentiating viable X-chromosome sperm and/or viable Y-chromosome bearing sperm.

26. The method of claim 25, wherein the step of orienting sperm is achieved in an orienting nozzle.

27. The method of claim 25, wherein the step of orienting sperm is achieved in a closed channel.

28. The method of claim 1, wherein the sperm sample is obtained from a mammal having a low sperm output.

29. The method of claim 28, wherein the minimum purity and productivity are established accounting for a low sperm count.

30. The method of claim 28, wherein the mammal comprises a young genomic sire.

* * * * *